United States Patent [19]

Albrecht et al.

[11] Patent Number: 5,147,871
[45] Date of Patent: Sep. 15, 1992

[54] ANTI-BACTERIAL CEPHALOSPORIN COMPOUNDS

[75] Inventors: Harry A. Albrecht, Towaco; Ka-Kong Chan, Hopatcong; Dennis D. Keith, Montclair, all of N.J.; Rudolf L. Then, Weil, Fed. Rep. of Germany; Manfred Weigele, North Caldwell, N.J.

[73] Assignee: Hoffman La-Roche, Inc., Nutley, N.J.

[21] Appl. No.: 803,757

[22] Filed: Dec. 5, 1991

Related U.S. Application Data

[63] Continuation of Ser. No. 68,092, Jun. 29, 1987, abandoned, which is a continuation-in-part of Ser. No. 881,555, Jul. 3, 1986, abandoned.

[51] Int. Cl.$^5$ .................. C07D 501/26; A61K 31/545
[52] U.S. Cl. ..................................... 514/202; 514/201; 514/206; 540/221; 540/222; 540/225; 540/226
[58] Field of Search ............... 540/221, 222, 225, 228; 514/201, 202, 206

[56] References Cited

U.S. PATENT DOCUMENTS

| Re. 32,491 | 9/1987 | Iwanami et al. | 540/221 |
|---|---|---|---|
| 3,971,778 | 7/1976 | Cook et al. | 260/243 C |
| 4,152,432 | 5/1979 | Heymes et al. | 424/246 |
| 4,202,893 | 5/1980 | Haynes et al. | 424/246 |
| 4,263,432 | 4/1981 | Iwanami et al. | 544/21 |
| 4,292,317 | 9/1981 | Pesson | 514/254 |
| 4,399,131 | 8/1983 | Dürckheimer | 540/222 |
| 4,404,373 | 9/1983 | Iwanami et al. | 544/21 |
| 4,468,394 | 8/1984 | Machida | 540/227 |
| 4,476,123 | 10/1984 | Labeeuw et al. | 424/246 |
| 4,501,743 | 2/1985 | Breuer et al. | 540/222 |
| 4,581,352 | 4/1986 | Foster et al. | 540/228 |
| 4,604,387 | 8/1986 | Labeeuw et al. | 514/206 |
| 4,608,373 | 8/1986 | Shibanuma et al. | 540/228 |
| 4,634,697 | 1/1987 | Hamashima | 540/222 |
| 4,647,556 | 3/1987 | Lattrell et al. | 544/29 |
| 4,656,166 | 4/1987 | Salhi et al. | 540/228 |
| 4,670,444 | 6/1987 | Grohe et al. | 514/300 |
| 4,753,952 | 6/1988 | Grohe et al. | 514/256 |
| 4,753,953 | 6/1988 | Masuzawa et al. | 514/312 |
| 4,758,567 | 6/1988 | Desideri et al. | 514/256 |
| 4,762,831 | 8/1988 | Grohe et al. | 514/230.2 |
| 4,762,845 | 8/1988 | Chu et al. | 514/312 |
| 4,767,762 | 8/1988 | Chu | 514/254 |
| 4,808,711 | 2/1989 | Shimizu et al. | 540/227 |
| 4,946,847 | 8/1990 | Jolidon et al. | 514/229.5 |

FOREIGN PATENT DOCUMENTS

| 036812 | 9/1981 | European Pat. Off. |
|---|---|---|
| 060745 | 9/1982 | European Pat. Off. |
| 121244 | 10/1984 | European Pat. Off. |
| 160546 | 6/1985 | European Pat. Off. |
| 187456 | 11/1985 | European Pat. Off. |
| 178980 | 4/1986 | European Pat. Off. |
| 192176 | 8/1986 | European Pat. Off. |
| 153709 | 4/1987 | European Pat. Off. |
| 335297 | 10/1989 | European Pat. Off. |
| 366189 | 5/1990 | European Pat. Off. |
| 366193 | 5/1990 | European Pat. Off. |
| 366640 | 5/1990 | European Pat. Off. |
| 366641 | 5/1990 | European Pat. Off. |
| 366643 | 5/1990 | European Pat. Off. |
| 3233376 | 3/1983 | Fed. Rep. of Germany |
| 2501209 | 9/1982 | France |
| 85278057 | 11/1984 | Japan |
| 1591439 | 6/1981 | United Kingdom |

OTHER PUBLICATIONS

J. Med. Chem., 5, 1063 (1962).
J. Med. Chem., 20(6), 791 (1977).
J. Med., Chem., 21(5), 485 (1978).
J. Med. Chem., 23(12), 1358 (1977).
J. Med. Chem., 27(3), 292 (1984).
J. Med. Chem., 27(9), 1103 (1984).
J. Med. Chem., 27(12), 1543 (1984).
J. Med. Chem., 28(11), 1558 (1985).
J. Med. Chem., 29(3), 394 (1986).
J. Med. Chem., 29(4), 445 (1986).
J. Med. Chem., 30(3), 504 (1987).
Tetrahedron, 23, 4719 (1967).
Synthesis, 787 (1979).
J. Heterocyclic Chem., 22, 1033 (1985).
Hackh's Chemical Dictionary, Grant, J., ed., 3rd Ed., McGraw-Hill, New York, pp. 78 and 814 (1944).
Biochem. J., 116, 371 (1970).
Antimicrobial Agents and Chemotherapy, 10(2), 249 (1976).

(List continued on next page.)

Primary Examiner—Nicholas S. Rizzo
Attorney, Agent, or Firm—George M. Gould; George W. Johnston; Alan P. Kass

[57] ABSTRACT

There are presented anti-bacterial cephalosporins having broad antimicrobial activity of the formula

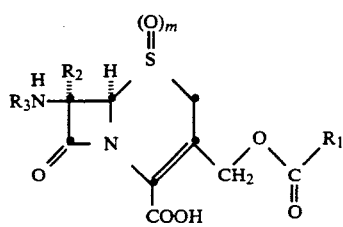

wherein $R_1$ is an antibiotically active quinolonyl; $R_2$ is selected from the group consisting of hydrogen, lower alkoxy, amino, lower alkylthio and amido; $R_3$ is selected from the group consisting of hydrogen, and acyl group, and m is 0, 1 or 2 and the readily hydrolysable esters or salts of these compounds and hydrates of the compounds of formula I or of their esters or salts.

45 Claims, No Drawings

OTHER PUBLICATIONS

Progress in Drug Research, 21, 9, 9 (1977).
The Chemistry and Biology of —Lactam Antibiotics, vol. 3, App. A pp. 379–392 (1982).
Antimicrobial Agents and Chemotherapy, 29(4), 581 (1985).
Agnew. Chem. Int. Ed. Engl., 24, 180 (1985).
Annual Reports in Medicinal Chemistry, 20, 145 (1985).
J. Med. Chem., 29(3), 394 (1986).
Annual Reports in Medicinal Chemistry, 21, 139 (1986).
Antimicrobial Agents and Chemotherapy, 31(4), 614 (1987).
American Journal of Medicine, 82, (Supp. 4A), 12 (Apr. 27, 1989).
J. Antimicrobial Chemotherapy, 17, 5 (1986).
Gary Weiss, *Barron's*, Mar. 10, 1986, pp. 34–64.
O'Callaghan et al., Antimicrobial Agents and Chemotherapy, 10(2), 245 (1976).
O'Callaghan et al., J. Bacteriology, 110(3), 988 (1972).
Mobashery et al., J. Amer. Chem. Soc., 108, 1685 (1986).
Mobashery et al., J. Bio. Chem., 261(17), 7879 (1986).
Russell et al., J. Bacteriology, 106(1), 65 (1971).
Decad et al., J. Bacteriology, 128(1), 325 (1976).
Nikaido, "The Role of Outer Membrane Permeability in the Sensitivity and Resistance of Gram-Negative Organisms to Antibiotics," in Drug Resistance in Bacteria, S. Mitsuhnshi (ed.), Thiene–Shetton Inc., NY (1982), 317–324.
Faraci et al., J. Amer. Chem. Soc., 106, 1489 (1989).
Jeffery et al., J. Org. Chem., 47(3), 587 (1982).
Litter, "Framacologia," 6a. Ed. El Ateneo, Buenos Aires (1980), p. 1517.
Albrecht et al., J. Med. Chem., 33, 77 (1990).
Albrecht et al., J. Med. Chem. 34, 669 (1991).
Albrecht et al., J. Med. Chem., 34, 2857 (1991).
"Burger's Medicinal Chemistry," Wolff, M. E., ed., Fourth Ed., Part II, pp. 83–85, 100–101, 107–108, 131–136 (1987).
Agnew. Chem. Int. Ed. Engl., 24, 180 (1985).

ANTI-BACTERIAL CEPHALOSPORIN COMPOUNDS

CROSS-REFERENCE TO RELATED APPLICATION

This is a continuation of copending application Ser. No. 07/068,092 filed on Jun. 29, 1987 now abandoned which is a continuation-in-part application of application Ser. No. 881,555, filed Jul. 3, 1986, now abandoned.

DESCRIPTION OF THE INVENTION

The present invention relates to anti-bacterial compounds of the formula

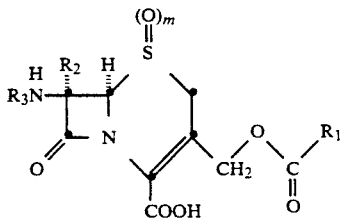

I wherein $R_1$ is a quinolonyl or an azaquinolonyl group; $R_2$ is selected from the group consisting of hydrogen, lower alkoxy, amino, lower alkylthio and amido; $R_3$ is selected from the group consisting of hydrogen, and an acyl group;
m is 0, 1 or 2 and the readily hydrolysable esters or salts of these compounds and hydrates of the compounds of formula I or of their esters or salts; m is preferably 0.

As used in this specification, the term "lower alkyl" or "alkyl" refers to both straight and branched chain saturated hydrocarbon groups having 1 to 8 and preferably, 1 to 4 carbon atoms, for example, methyl, ethyl, propyl, isopropyl, tertiary butyl and the like.

As used herein, the term "lower alkoxy" refers to a straight or branched chain hydrocarbonoxy group wherein the "alkyl" portion is a lower alkyl group as defined hereinbefore. Exemplary are methoxy, ethoxy, propoxy and the like.

The term "halo" or "halogen" as used herein represents all four forms thereof, i.e. chloro, bromo, iodo or fluoro unless otherwise specified.

The term "acyl", as used in conjunction with $R_3$ herein, means and includes all organic radicals derived from an organic acid (i.e., a carboxylic acid) by removal of the hydroxyl group. Although the group $R_3$ may be any one of many acyl radicals, certain acyl groups are preferred.

Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), Belgian patent 866,038 published Oct. 17, 1978, Belgian patent 867,994, published Dec. 11, 1978, U.S. Pat. Nos. 4,152,432, issued May 1, 1979, 3,971,778, issued Jul. 27, 1976, and 4,173,199, issued Oct. 23, 1979. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R^5$ is alkyl, cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

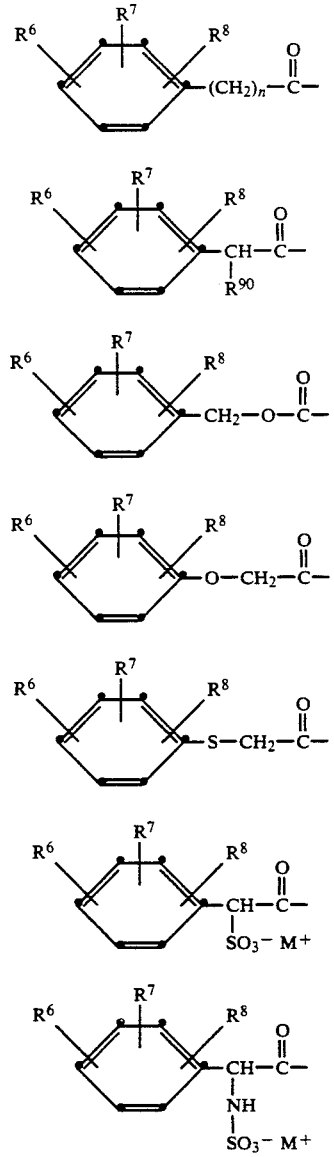

wherein n is 0, 1, 2 or 3; $R^6$, $R^7$, and $R^8$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and $R^{90}$ is amino, acylamino, hydroxyl, a carboxyl salt, protected carboxy, such as benzyloxycarbonyl, formyloxy or azido.

Preferred carbocyclic aromatic acyl groups include those having the formula

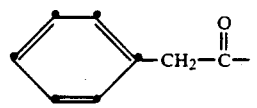

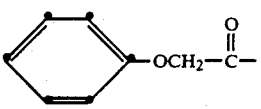

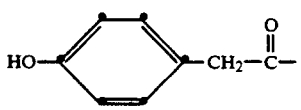

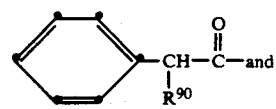

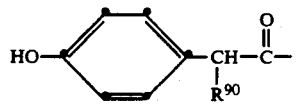

($R^{90}$ is preferably an amino group, a hydroxy group, or a carboxyl salt or sulfo salt).

Examples of other acyl groups suitable for the purposes of the present invention are
-sulfophenylacetyl,
-hydroxysulfonyloxyphenylacetyl,
-sulfamoylphenylacetyl,
-(phenoxycarbonyl)phenylacetyl,
-(p-tolyloxycarbonyl)phenylacetyl,
-formyloxyphenylacetyl,
-carboxyphenylacetyl,
-formylaminophenylacetyl,
-benzyloxycarbonylphenylacetyl;
2-(N,N-dimethylsulfamoyl)-2-phenylacetyl,
2-bromo-2-thienylacetyl, etc.

(c) Heteroaromatic groups having the formula

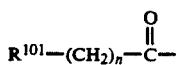

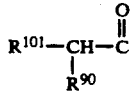

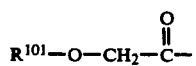

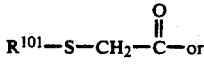

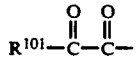

wherein n is 0, 1, 2 or 3; $R^{90}$ is as defined above; and $R^{101}$ is a substituted or unsubstituted 5-, 6-or 7-membered heterocyclic ring containing 1, 2, 3 or 4 (preferably 1 or 2) nitrogen, oxygen or sulfur atoms. Exemplary heterocyclic rings are thienyl, furyl, pyrrolyl, pyridinyl, pyrazinyl, thiazolyl, pyrimidinyl and tetrazolyl. Exemplary substituents are halogen, hydroxyl, nitro, amino, cyano, trifluoromethyl, alkyl of 1 to 4 carbon atoms, or alkoxy of 1 to 4 carbon atoms.

Preferred heteroaromatic acyl groups include those groups of the above formulas wherein $R^{101}$ is 2-amino-4-thiazolyl, 2-amino-5-halo-4-thiazolyl, 4-aminopyridin-2-yl, 2-amino-1,3,4-thiadiazol-5-yl, 2-thienyl, 2-furanyl, 4-pyridinyl or 2,6 dichloro-4-pyridinyl.

(d) [[(4-Substituted-2,3-dioxo-1-piperazinyl)carbonyl-]amino] substituted acetyl groups having the formula

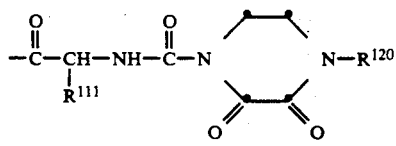

wherein $R^{111}$ is alkyl, hydroxyalkyl or an aromatic group (including carbocyclic aromatics) such as those of the formula

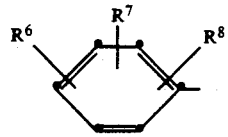

wherein $R^6$, $R^7$, and $R^8$ are as previously defined and heteroaromatics as included within the definition of $R^{101}$; and $R^{120}$ is alkyl, substituted alkyl (wherein the alkyl group is substituted with one or more halogen, cyano, nitro, amino or mercapto groups) e.g. 4-lower alkyl (preferably ethyl or methyl)-2, 3-dioxo-1-piperazinecarbonyl-D-phenylglycyl.

(e) (Substituted oxyimino) substituted acetyl groups having the formula

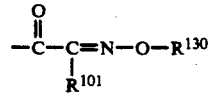

wherein $R^{101}$ is as defined above and $R^{130}$ is hydrogen, lower alkyl and $C_3$-$C_7$ cycloalkyl or substituted lower alkyl (wherein the alkyl group is substituted with 1 or more halogen, cyano, nitro, amino, mercapto, lower alkylthio, aromatic group (as defined by $R^{111}$), carboxyl (including salts thereof), amido, lower alkoxycarbonyl, phenylmethoxycarbonyl, diphenylmethoxycarbonyl, hydroxyalkoxyphosphinyl, dihydroxyphosphinyl, hydroxy (phenylmethoxy) phosphinyl, diloweralkoxyphosphinyl substituents), carboxyl lower alkyl or carboxyl-3-7-cycloalkyl.

Examples of

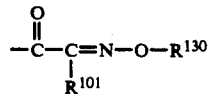

grouping are
2-[(2-chloroacetamidothiazol-4-yl)-2-[(p-nitrobenzyloxycarbonyl]methoxyimino]acetyl
2-(2-chloroacetamidothiazol-4-yl)-2-methoxyiminoacetyl,
2-(2-aminothiazol-4-yl)-2-isopropoxy-iminoacetyl,
2-(2-aminothiazol-4-yl)-2-methoxyiminoacetyl, 2-(2-aminothiazol-4-yl)-2-hydroxyiminoacetyl,
2-thienyl-2-methoxyiminoacetyl,
2-furyl-2-methoxyiminoacetyl,
2-(4-hydroxyphenyl)-2-methoxyiminoacetyl,
2-phenyl-2-methoxy-iminoacetyl,
2-phenyl-2-hydroxyiminoacetyl,
2-thienyl-2-hydroxyiminoacetyl,
2-thienyl-2-(dichloroacetyloxyimino)acetyl,
2-[4-(γ-D-glutamyloxy)phenyl]-2-hydroxyiminoacetyl,
2-[4-(3-amino-3-carboxypropoxy)phenyl]-2-hydroxyiminoacetyl,
2-(5-chloro-2-chloroacetamidothiazol-4-yl)-2-methoxyiminoacetyl,
2-(5-chloro-2-aminothiazol-4-yl)-2-methoxyiminoacetyl,
2-[2-(t-butoxycarbonyl)isopropoxyimino]-2-(2-sulfoamino-thiazol-4-yl)acetyl,
2-[2-(t-butoxycarbonyl) isopropoxyimino]-2-(2-triphenyl-methylamino-thiazol-4-yl) acetyl,
2-(2-chloroacetamidothiazol-4-yl)-2-isopropoxyiminoacetyl,
2-methoxyimino-2-(2-sulfoaminothiazol-4-yl)acetyl,
2-[(2-aminothiazol-4-yl)-2-carboxymethoxyimino]acetyl
2-[2-(2-mesylaminothiazol-4-yl)-2-isopropoxyiminoacetyl,
2-(2-imino-3-mesyl-4-thiazolin-4-yl)-2-isopropoxyiminoacetyl,
2-[(2-aminothiazol-4-yl)-2-(carboxyisopropoxyimino)acetyl etc.

(f) (Acylamino) substituted acetyl groups having the formula

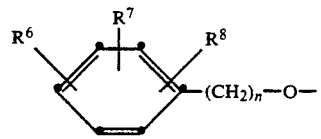

wherein $R^{111}$ is as defined above
and $R^{140}$ is

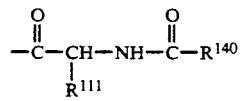

(where $R^6$, $R^7$, $R^8$ and n are as previously defined), hydrogen, lower alkyl, substituted lower alkyl, amino, alkylamino, (cyanoalkyl) amino, or acylamino.

Preferred (acylamino) substituted acetyl groups of the above formula include those groups wherein $R^{140}$ is amino, or acylamino. Also preferred are those groups wherein $R^{111}$ is phenyl or 2-thienyl.

(g) [[[3-Substituted-2-oxo-1-imidazolidinyl]carbonyl]amino] substituted acetyl groups having the formula

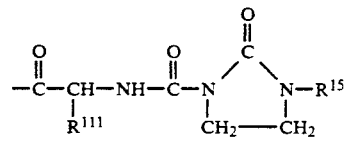

wherein $R^{111}$ is as defined above and $R^{15}$ is hydrogen, alkylsulfonyl, arylmethyleneamino (i.e., —N═CHR$^{111}$ wherein $R^{111}$ is as defined above).

(wherein $R^{16}$ is hydrogen, alkyl or halogen substituted alkyl), aromatic group (as defined by $R^{111}$ above), alkyl or substituted alkyl (wherein the alkyl group is substituted with one or more halogen, cyano, nitro, amino or mercapto groups).

Preferred [[[3-substituted-2-oxo-1-imidazolidinyl]carbonyl]amino] substituted acetyl groups of the above formula include those wherein $R^{111}$ is phenyl or 2-thienyl. Also preferred are those groups wherein $R^{15}$ is hydrogen, methylsulfonyl, phenylmethyleneamino or 2-furylmethyleneamino.

As used herein the quinolonyl or azaquinolonyl substituent $R_1$ include, among others, compounds of the formulas

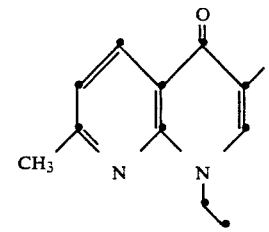

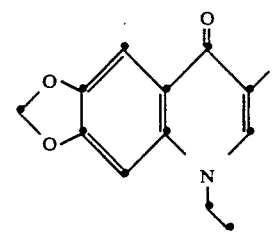

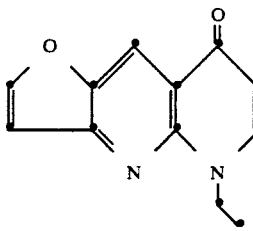

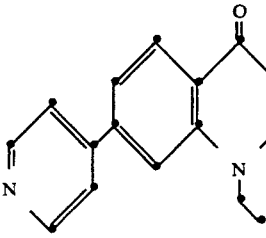

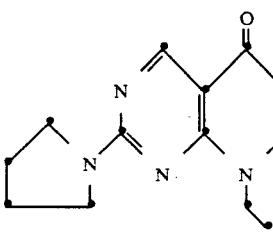

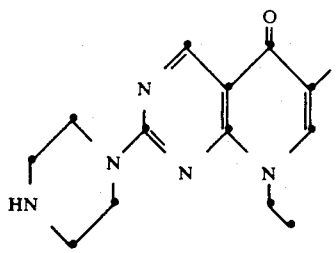
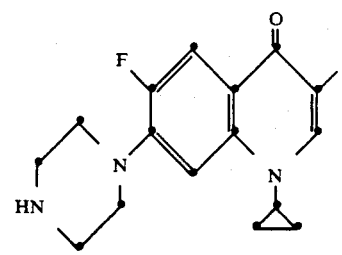
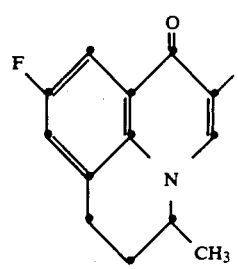
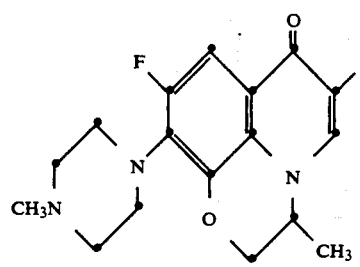
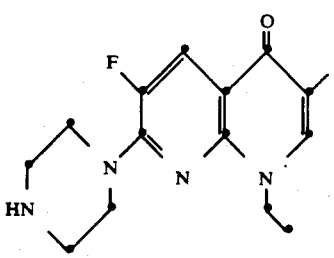
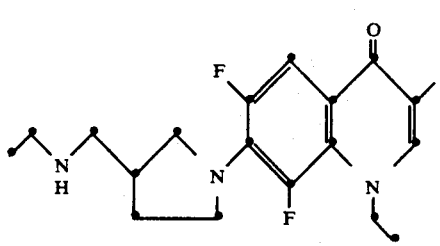
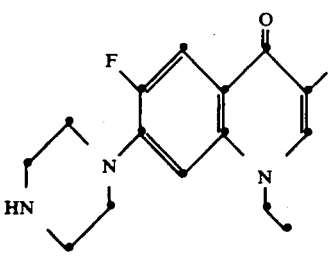
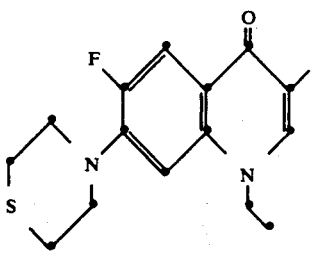
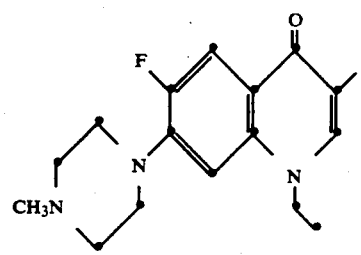
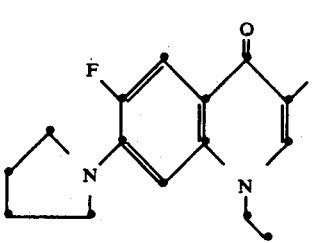
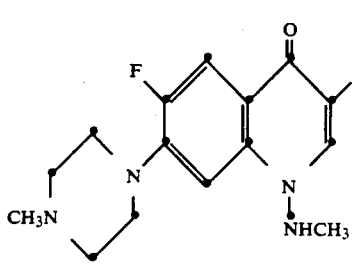
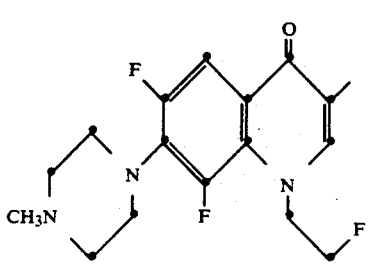

-continued

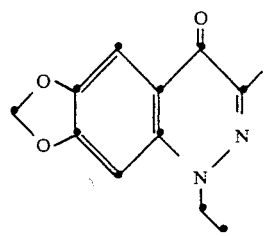

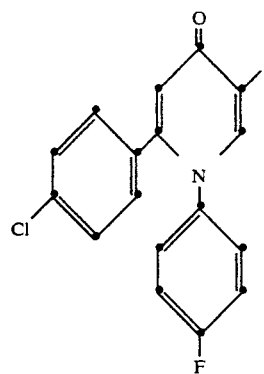

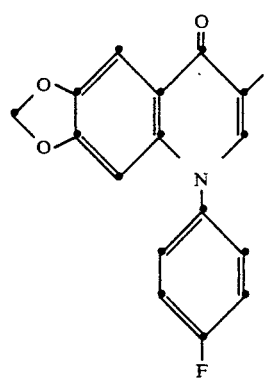

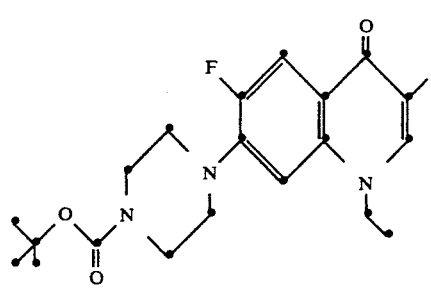

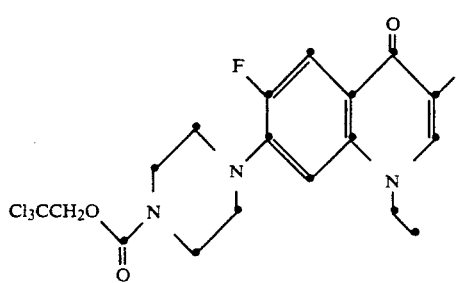

-continued

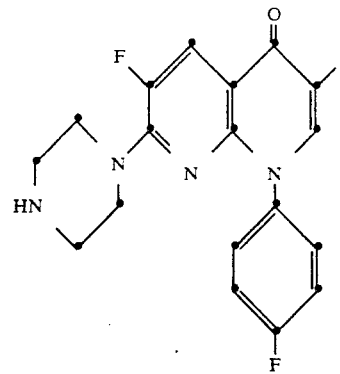

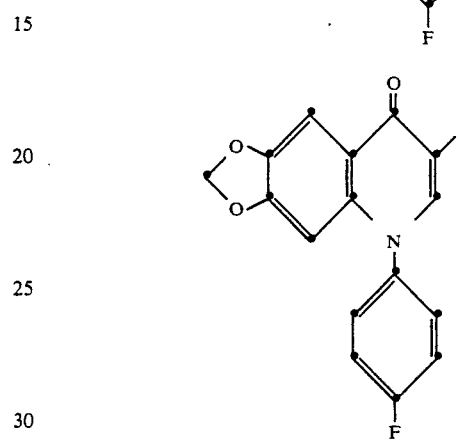

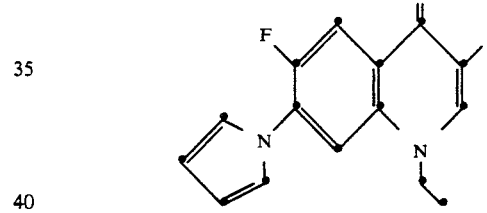

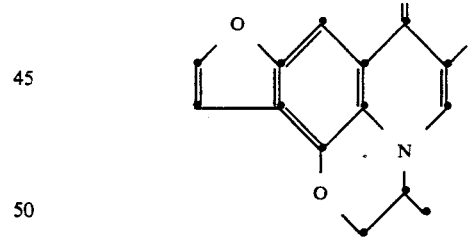

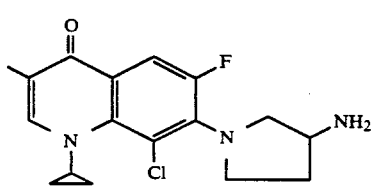

By the term "aryl" is meant a substituted or unsubstituted aromatic moiety, such as, phenyl, tolyl, xylyl, mesityl, (cumenyl) naphthyl and the like wherein said aryl group may have 1 to 3 suitable substituents, such as, halo (fluoro, chloro, bromo, etc.), hydroxy and the like.

By the term or "lower alkanoyl" or "alkanoyl" as utilized herein is intended a moiety of the formula

wherein R$^{25}$ is C$_1$ to C$_6$ lower alkanoic acid, e.g. acetyl, formyl, propionyl, butyryl and the like.

By the term "substituted phenyl" is meant phenyl mono- or di-substituted by halo(chloro, bromo, fluoro, etc.), lower alkyl, amino, nitro or trifluoromethyl.

By the term "substituted alkyl" is meant a "lower alkyl" moiety substituted by, for example, halo(chloro, fluoro, bromo, etc.)trifluoromethyl, amino, cyano, etc.

By the term "lower alkenyl" is meant straight or branched chain hydrocarbon groups which contain an olefinic double bond having 2 to 6 carbon atoms i.e. the radical of compounds of the formula C$_n$H$_{2n}$ wherein n is 2 to 6 e.g. alkyl, vinyl etc.

By the term "aralkyl" is meant a hydrocarbon group having both aromatic and aliphatic structures, that is, a hydrocarbon group in which a lower alkyl hydrogen atom is substituted by a monocyclic aryl group, e.g. phenyl, tolyl, etc.

The expression 5 or 6 membered heterocyclic atoms containing 1-3 hetero atoms selected from the group consisting of O, N and S is intended to represent the following groups: pyridyl, piperidyl, piperidino, N-oxido-pyridyl, pyrimidyl, piperazinyl, pyrolidinyl, pyridazinyl, N-oxide-pyridazinyl, etc. a 5-membered nitrogen-containing hetero ring e.g. pyrazolyl, imidazolyl thiazolyl, 1,2,3-thiadiazolyl, 1,2,4-thiadiazolyl, 1,3,4-thiadiazolyl, 1,2,4-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, etc., and others. Each of these hetero rings may be further substituted and, as the substituents, there may be mentioned for example, lower alkyls such as methyl, ethyl, propyl, etc. lower alkoxys such as methoxy, ethoxy, etc., halogens such as chlorine, bromine, etc., halogen substituted alkyls such as trifluoromethyl, trichloroethyl, aminomethyl, ethylaminomethyl, etc., amino, mercapto, hydroxyl, carbamoyl, or carboxyl group, etc.

By the term "cycloloweralkyl" is meant a 3-6 membered saturated carbocyclic moiety, e.g. cyclopropyl, cyclobutyl, cyclohexyl, etc.

As readily hydrolyzable esters of the compounds of formula I there are to be understood compounds of formula I, the carboxy group(s) of which (i.e. the 2-carboxy group) is/are present in the form of readily hydrolyzable ester groups. Example of such esters, which can be of the conventional type, are the lower alkanoyloxyalkyl esters (e.g. the acetoxymethyl, pivaloyloxymethyl, 1-acetoxyethyl and 1-pivaloyloxyethyl ester), the lower alkoxycarbonyloxyalkyl esters (e.g. the methoxycarbonyloxymethyl, 1-ethoxycarbonyloxyethyl and 1-isopropoxycarbonyloxyethyl ester), the lactonyl esters (e.g. the phthalidyl and thiophthalidyl ester), the lower alkoxymethyl esters (e.g. the methoxymethyl ester) and the lower alkanoylaminomethyl esters (e.g. the acetamidomethyl ester). Other esters (e.g. the benzyl and cyanomethyl esters) can also be used.

Example of salts of the compounds of formula I are alkali metal salts such as the sodium and potassium salt, the ammonium salt, alkaline earth metal salts such as the calcium salt, salts with organic bases such as salts with amines (e.g. salts with N-ethyl-piperidine, procaine, dibenzylamine, N,N'-dibenzylethylenediamine, alkylamines or dialkylamines) as well as salts with amino acids such as, for example, salts with arginine or lysine.

The compounds of formula I when they contain a basic functional group such as an amine, also form addition salts with organic or inorganic acids. Examples of such salts are hydrohalides (e.g. hydrochlorides, hydrobromides and hydroiodides) as well as other mineral acid salts such as sulphates, nitrates, phosphates and the like, alkylsulphonates and monoarylsulphonates such as ethanesulphonates, toluenesulphonates, benzenesulphonates and the like and also other organic acid salts such as acetates, tartrates, maleates, citrates, benzoates, salicylates, ascorbates and the like.

The compounds of formula I as well as their salts and readily hydrolyzable esters can be hydrates. The hydration can be effected in the course of the manufacturing process or can occur gradually as a result of hygroscopic properties of an initially anhydrous product.

A preferred class of compounds are of the formula

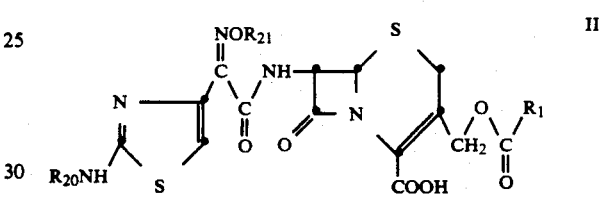

wherein R$_1$ is as above, R$_{20}$ is hydrogen or an amino protecting group such as trityl or chloroacetyl, R$_{21}$ is hydrogen, lower alkyl, or a group of the formula

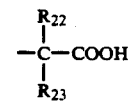

wherein R$_{22}$ and R$_{23}$ are selected from the group consisting of hydrogen and lower alkyl, or R$_{22}$ and R$_{23}$ taken together with the carbon atom to which they are attached form a 3-7 carbocyclic ring, e.g., cyclopropyl, cyclobutyl or cyclopentyl. Still more preferred are compounds of the formula II in which R$_{20}$ is hydrogen, and R$_{21}$ is methyl or a group of the formula

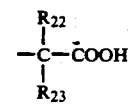

wherein R$_{22}$ and R$_{23}$ are selected from the group consisting of hydrogen and methyl.

Preferably, the

grouping is in the syn-form, i.e., the Z-form.

R$_1$ is preferably of the formula

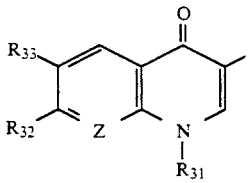

wherein Z represents

or N, $R_{30}$ represents hydrogen or halogen;

$R_{31}$ represents hydrogen, lower alkyl, lower alkenyl, $C_3$-$C_7$ cycloalkyl, halo lower alkyl or mono, di and tri-halophenyl;

$R_{30}$ and $R_{31}$ when taken together represents lower alkylene of 3-5 carbon atoms, a lower alkylene mono-oxy group of 2-4 carbon atoms or a lower alkylene dioxy group having 1-2 carbon atoms;

$R_{32}$ represents hydrogen, halogen, lower alkyl, a 5 or 6 membered heterocyclic ring containing 1-3 hetero atoms selected from the group consisting of O, N and S, which may be substituted;

$R_{33}$ represents hydrogen and halogen; and $R_{32}$ and $R_{33}$ when taken together represents a $C_1$-$C_4$ lower alkylene dioxy group.

In a preferred embodiment, Z is

wherein $R_{30}$ is hydrogen, chlorine or fluorine, most preferably hydrogen or fluorine;

$R_{31}$ is lower alkyl, most preferably, ethyl or halogen lower alkyl, most preferably, fluoroethyl or $C_3$-$C_7$-cycloalkyl, most preferably, cyclopropyl;

$R_{32}$ is lower alkyl, most preferably, methyl or piperizinyl which may be substituted on the 4-nitrogen atom with a lower alkyl group, most preferably methyl and $R_{33}$ is hydrogen or chlorine or fluorine, more preferably hydrogen or fluorine, and still more preferably fluorine.

Specifically preferred are compounds of the formula

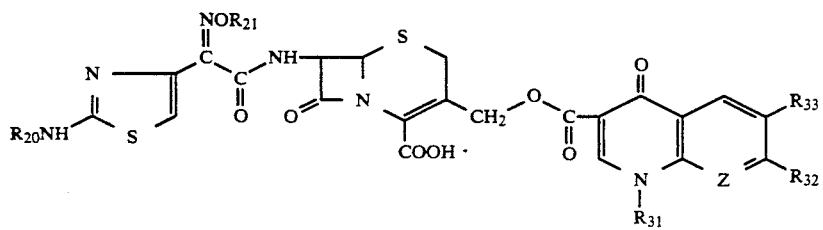

wherein $R_{20}$, $R_{21}$, Z, $R_{31}$, $R_{32}$ and $R_{33}$ are as above and are preferably as identified hereinabove.

Compounds of the Formula I, their salts and esters and hydrates of those compounds can be used as agents to combat bacterial infections (including urinary tract infections and respiratory infections) in mammalian species, e.g., dogs, cats, horses, etc., and humans. The cephalosporins exhibit activity against a broad range of both gram-negative and gram-positive bacteria.

The in vitro activity of the compounds of the present invention as measured by the Minimum Inhibitory Concentration in micrograms/ml utilizing the Agar Well Diffusion Method or Broth Dilution Method against a variety of Gram-positive and Gram-negative organisms is as follows:

Compound A: [6R-(6alpha,7beta)]-3-[[[(1-Ethyl-1,4-dihydro-7-methyl-4-oxo-1,8-naphthydrin-3-yl)carbonyl]oxy]methyl]-8-oxo-7-[(phenoxyacetyl)amino]-5-thia-1-azabicyclo[4.2.0]oct-2-ene-2-carboxylic acid hydrate Compound B: [6R-(6alpha,7beta)]-3-[[[(5-Ethyl-5,8-dihydro-8-oxo-1,3-dioxolo[4,5-g]quinolin-7-yl)carbonyl] oxy]methyl]-8-oxo-7-[(phenoxyacetyl)amino]-5-thia-1-azabicyclo[4.2.0]oct-2-ene-2-carboxylic acid monosodium salt Compound C: [6R-(6alpha,7beta)(Z)]-7-[[(2-Amino-4-thiazolyl) (methoxyimino)acetyl]amino]-3-[[[(1-ethyl-1,4-dihydro-7-methyl-4-oxo-1,8-naphthyridin-3-yl) carbonyl]oxy]methyl]-8-oxo-5-thia-1-azabicyclo [4.2.0]oct-2-ene-2-carboxylic acid sodium salt.

Compound D: [6R-(6alpha,7beta)(Z)]-7-[[(2-Amino-4-thiazolyl) (methoxyimino)acetyl]amino]-3-[[[(5-ethyl-5,8-dihydro-8-oxo-1,3-dioxolo[4,5-g]quinolin-7-yl) carbonyl]oxy]methyl]-8-oxo-5-thia-1-azabicyclo [4.2.0]oct-2-ene-2-carboxylic acid sodium salt Compound E: [6R-(6alpha,7beta)]-3-[[[[1-Ethyl--6-fluoro-1,4-dihydro-7-(4-formyl-1-piperazinyl)-4-oxo-quinolin-3-yl]-carbonyl]oxy]methyl-8-oxo-7-[(phenoxyacetyl)amino]-5-thia-1-azabicyclo[4.2.-0]oct-2-ene-2-carboxylic acid sodium salt Compound F: [6R-(6alpha,7beta)]-3-[[[(5-Ethyl-5,8-dihydro-8-oxo-1,3-dioxolo[4,5-g]quinolin-7-yl)carbonyl] oxy]methyl]-8-oxo-7-[(2-thienylacetyl)amino]-5-thia-1-azabicyclo-[4.2.0]oct-2-ene-2-carboxylic acid sodium salt Compound G: [6R-(6alpha,7beta)]-3-[[[1-Ethyl-6-fluoro-1,4-dihydro-7-(4-formyl-1-piperazinyl)-4-oxoquinolin-3-yl]-carbonyl]oxy]methyl]-7-[(2-thienylacetyl)amino]-5-thia-1-azabicyclo[4.2.0]oct-2-ene-2-carboxylic acid sodium salt Compound H: [6R-(6alpha,7beta)]-3-[[[[1-Ethyl-6-fluoro-1,4-dihydro-7-(1-pyrrolidinyl)-4-oxo-quinolin-3-yl]carbonyl]oxy]methyl]-8-oxo-7-[(phenoxyacetyl) amino]-5-thia-1-azabicyclo[4.2.0]oct-2-ene-2-carboxylic acid sodium salt Compound I: [6R-(6alpha,7beta)(Z)]-7-[[(2-Amino-4-thiazolyl) (methoxyimino)acetyl]amino]-3-[[[[1-ethyl-6-fluoro-1,4-dihydro-7-(1-pyrrolidinyl)-4-oxoquinolin-3-yl]-carbonyl]oxy]methyl]-8-oxo-5-thia-1-azabicyclo[4.2.0]oct-2-ene-2-carboxylic acid sodium salt

| | In vitro MIC (μg/ml) Broth Dilution Method | | | | | | | | |
|---|---|---|---|---|---|---|---|---|---|
| | Compounds | | | | | | | | |
| Culture | A | B | C | D | E | F | G | H | I |
| E. coli 48 | 32 | 2 | 0.5 | 0.25 | 8 | 2 | 8 | 32 | 0.5 |
| K. pneumoniae A | 16 | 1 | 0.5 | 0.25 | 2 | 1 | 4 | 32 | 0.5 |
| E. cloacae 9570A | 64 | 2 | 2 | 1 | 8 | 2 | 8 | 32 | 2 |
| E. cloacae 948-1 | — | 2 | 8 | 1 | 8 | 1 | 8 | 32 | 4 |
| E. cloacae 2367-2 | — | 1 | 16 | 2 | 4 | 1 | 32 | 32 | 4 |
| E. cloacae 7099 | 16 | 0.5 | 8 | 0.5 | 2 | 0.5 | 2 | 2 | 2 |
| E. cloacae 214 | 128 | 2 | 8 | 0.5 | 8 | 2 | 64 | 32 | 4 |
| P. vulgaris ATCC 6380 | 8 | 0.5 | 0.25 | 0.063 | 4 | 0.5 | 4 | 32 | 0.5 |
| P. mirabilis 190 | 8 | 0.5 | 0.16 | 0.008 | 0.5 | 0.5 | 4 | 0.5 | 0.031 |
| S. marcescens SM | 16 | 1 | 1 | 0.5 | 4 | 1 | 4 | 32 | .1 |
| P. aeruginosa Stone 130 | 128 | 32 | 128 | 16 | 16 | 32 | 32 | 32 | 8 |
| P. aeruginosa 503-56 | 128 | 64 | 128 | 32 | 32 | 64 | 64 | 64 | 32 |
| S. aureus Smith | 0.25 | 0.25 | 2 | 2 | 0.063 | 0.25 | 0.25 | 0.25 | 0.25 |
| S. aureus 95 | — | 4 | 8 | 4 | 2 | 4 | 4 | 0.5 | 0.5 |

For combatting bacterial infections in mammals, a compound of this invention can be administered to a mammal in need thereof an amount of about 5 mg/kg/day to about 500 mg/kg/day, preferably about 10 mg/kg/day to 100 mg/kg/day, most preferably about 10 mg/kg/day to about 55 mg/kg/day.

All modes of administration which have been used in the past to deliver penicillins and cephalosporins to the site of the infection are also contemplated for use with the novel family of the dual action cephalosporins of this invention. Such methods of administration include intravenous, intramuscular and enterally e.g. as a suppository.

The following reaction schemes set forth the methods and intermediates useful in producing the novel end products of formula I.

In the following reaction sequences where a substituent group is present which may be attacked during the reaction it should be in protected form utilizing well known protecting groups. For example amino groups may be protected with easily removable protective groups employed in peptide chemistry, such as an alkoxycarbonyl group, e.g., t-butoxycarbonyl, etc., a substituted alkoxycarbonyl group, e.g., trichloroethoxycarbonyl, etc., a substituted alkycarbonyl, e.g., monochloromethylcarbonyl, or a substituted aralkyloxycarbonyl group, e.g., p-nitrobenzyloxycarbonyl.

A preferred protecting group is tert.-butyloxycarbonyl (t-BOC).

As ester protecting groups one may utilize an ester form which can be easily converted into a free carboxyl group under mild conditions, the ester protecting group being exemplified by, for example, t-butyl, p-nitrobenzyl, benzhydryl, allyl, etc.

The following reaction schemes set forth novel methods and intermediates to produce the compound of claim 1.

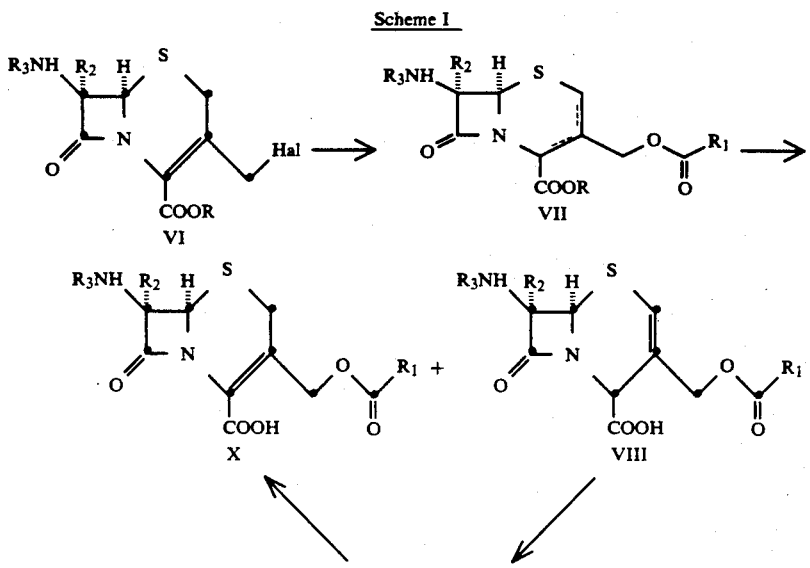

Scheme I

Scheme I

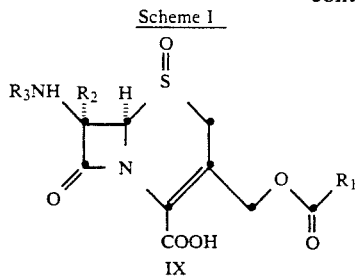

IX

R₁, R₂ and R₃ are as defined above.

In the above reaction scheme depending on the ester protecting group chosen and the halogen employed, the double bond in the cephem ring may be Δ3 or Δ2 with regard to the sulfur atom due to isomerization. The mixed product may be purified, if necessary, to only the desired isomer by production of the sulfoxide (IX) and subsequent reduction of that compound or purified by separation of the two components.

SCHEME I

VI→VII

The compound of formula VI which is known or made by analogy, see, for Example U.S. Pat. Nos. 4,406,899 and 4,266,049 is reacted with the salt of the chosen quinolone. The reaction is carried out in a nonhydroxylic solvent, such as, dimethylformamide, methylene chloride or N,N-dimethylacetamide. Other nonhydroxylic solvents may also be utilized. Suitable salts of the quinolone acid are, for example, sodium, potassium, cesium, tetrabutylammonium, or tetramethylammonium. Hal is a halogen, preferably bromine or iodine. The reaction is run at about 0° C. to 80° C. with about room temperature as preferred.

VII→VIII or X

The compound of formula VII thereafter is deprotected using agents compatible with the ester protecting group utilized. For example the following reagents and their corresponding compatible ester are utilized: paranitrobenzyl removed by hydrolysis in the presence of sodium sulfide at about or below 0° C. to room temperature in a solvent, such as, dimethylformamide (aqueous); t-butyl ester removed by reaction with trifluoroacetic acid in the presence of anisole at about 0° C. to room temperature with or without a cosolvent, such as, methylene chloride, or allyl esters removed by a palladium (O) catalyzed transallylation reaction in the presence of the sodium or potassium salt of 2-ethyl hexanoic acid, see for example J. Org. Chem. 1982, 47, 587.

VIII→IX

If isomerization of the double bond occurs, the compound of formula VIII is thereafter oxidized with a peracid, such as, methachloroperbenzoic acid in a solvent, such as, methylene chloride at a reaction temperature of about −20° C. to 40° C., preferably at about 0° C.

IX→1

The compound of formula IX is thereafter reduced to the desired end product I utilizing one of a variety of reactions. For example, treatment with phosphorus trichloride in DMF or trifluoroacetic anhydride in the presence of sodium iodide in acetone/methylene chloride. The reaction temperature for both of the above reactions can be carried out at about 0° C. to −20° C. with about 0° C. preferred.

EXAMPLE 1

Mixture of [6R-(6α,7β)]-3-[[[(1-ethyl-1,4-dihydro-7-methyl-4-oxo-1,8-naphthyridin-3-yl)carbonyl]oxy]methyl]-8-oxo-7-[(phenoxyacetyl)amino]-5-thia-1-azabicyclo[4.2.0]oct-2-ene-2-carboxylic acid(4-nitrophenyl)methyl ester and [2R-(2α,6α,7β)]-3-[[[(1-ethyl-1,4-dihydro-7-methyl-4-oxo-1,8-naphthyridin-3-yl)carbonyl]oxy]methyl]-8-oxo-7-[(phenoxyacetyl)amino]-5-thia-1-azabicyclo[4.2.0]oct-3-ene-2-carboxylic acid (4-nitrophenyl)methyl ester.

A solution of 22.4 g (0.040 mol) of [6R-(6α,7β)]-3-(bromomethyl)-8-oxo-7-[(phenoxyacetyl)amino]-5-thia-1-azabicyclo[4.2.0]oct-2-ene-2-carboxylic acid (4-nitrophenyl)methyl ester and 10.1 g (0.040 mol) of 1-ethyl-1,4-dihydro-7-methyl-4-oxo-1,8-naphthyridine-3-carboxylic acid sodium salt in 200 mL of dry DMF was stirred under argon for 5 hours. The solvent was evaporated under reduced pressure. A solution of the residue in ethyl acetate was washed with brine, decolorized with charcoal, dried (Na₂SO₄), and concentrated to a low volume under reduced pressure, whereupon the titled end products crystallized. The mother liquor was purified by column chromatography on 800 g of neutral silica gel (0.063–0.200 mm, 70–230 mesh ASTM) using ethyl acetate as eluant. The appropriate fractions were combined and crystallized from ethyl acetate to obtain additional end products. The mixture of isomers was used for the subsequent reaction. Pure Δ3 ester was obtained by fractional crystallization from ethyl acetate, and the Δ2 ester was isolated by preparative TLC of the mother liquor on Merck PLC plates (Silica Gel 60F-254). Physical properties of the two isomers were as follows:

Δ3-Isomer: 1R(KBr) 3405, 1785, 1735, 1697, 1637, 1520, 1348 cm⁻¹; mass spectrum m/z 714 (M⁺+H), 736 (M⁺+Na)

Δ2-Isomer: 1R(KBr) 3560, 3480, 3415, 1780, 1745, 1693, 1620, 1520 cm⁻¹; mass spectrum m/z 713 (M⁺).

EXAMPLE 2

[2R-(2α,6α,7β)]-3-[[[(1-Ethyl-1,4-dihydro-7-methyl-4-oxo-1,8-naphthyridin-3-yl)carbonyl]oxy]methyl]-8-oxo-7-[(phenoxyacetyl)amino]-5-thia-1-azabicyclo[4.2.0]oct-3-ene-carboxylic acid A solution of 2.80 g (0.0116 mol) of sodium sulfide hydrate in 20 mL of water was added dropwise to a solution of 6.11 g (0.00856 mol) of a mixture of the two isomers of Example 1 in 45 mL of DMF, at −5° to −10° C. After 35 minutes, the mixture was acidified to pH 3.5 by addition of N HCL, to precipitate a gum.

Upon addition of 50 mL of ethyl acetate and 50 mL of ether, the gum solidified. After filtration, washing with water and ether, and drying at 50° C. under reduced pressure over $P_2O_5$, the end product was obtained. Addition of more ether to the filtrate produced additional precipitate which was filtered, and dissolved in aqueous $NaHCO_3$. The aqueous solution was washed with ethyl acetate, and then acidified to pH 3.5. A solution of the precipitated gum in methylene chloride was filtered, washed with water, dried ($Na_2SO_4$) and concentrated under reduced pressure to obtain additional end product: IR(KBr) 3420, 3300, 1773, 1720 cm$^{-1}$; mass spectrum m/z 579 (M$^+$ +H).

EXAMPLE 3

[6R-(6α,7β)]-3-[[[(1-Ethyl-1,4-dihydro-7-methyl-4-oxo-1,8-naphthyridin-3-yl)carbonyl]oxy]methyl]-8-oxo-7-[(phenoxyacetyl)amino-5-thia-1-azabicyclo[4.2.0]oct-2-ene-2-carboxylic acid S-oxide A solution of 0.986 g (85% pure, 0.00486 mol) of m-chloroperbenzoic acid in 15 mL of methylene chloride was added dropwise to a stirred suspension of 2.55 g (0.00442 mol) of the end product of Example 2 in 60 mL of methylene chloride at 0° C. The mixture was stirred four hours at 0°, and filtered. The solid was washed with methylene chloride, and dried under reduced pressure to obtain end product: IR(KBr) 3360, 1794, 1723, 1684, 1637, 1017 cm$^{-1}$; mass spectrum m/z 595 (M$^+$ +H)

EXAMPLE 4

[6R-(6α,7β)]-3-[[[(1-Ethyl-1,4-dihydro-7-methyl-4-oxo-1,8-naphyridin-3-yl)carbonyl]oxy]methyl]-8-oxo-7-[(phenoxyacetyl)-amino]-5-thia-1-azabicyclo[4.2.0]oct-2-ene-2-carboxylic acid hydrate To a solution of 1.64 g (0.0109 mol) of sodium iodide in 40 mL of dry acetone and 20 mL of methylene chloride was added 1.30 g (0.00219 mol) of the end product of Example 3. The stirred suspension was cooled and 1.75 mL (0.0124 mol) of trifluoroacetic anhydride was added at 0° C. After 30 minutes, aqueous $NaHCO_3$ was added, to pH 6.0. Then N HCl was added to pH 3.5, and a small insoluble portion removed by filtration. The organic phase was washed with aqueous sodium sulfite, dried ($Na_2SO_4$), and concentrated under reduced pressure. The residual solid was washed with ether, and reprecipitated from methylene chloride solution by addition of ether to obtain end product.

Alternatively, a mixture of 0.435 g (0.73 mmol) of the end product of Example 3 and 7 mL of dry DMF was stirred and cooled to −12° C., and 0.128 mL (1.4 mmol) of phosphorus trichloride was added. After 7 minutes, an additional 0.027 mL of phosphorus trichloride was added. The mixture was stirred for 6.5 minutes. A cold solution of 0.428 g (5.1 mmol) of sodium bicarbonate in 70 mL of water was then added. The precipitate was filtered, washed with water, and dried under reduced pressure over $P_2O_5$ to obtain end product. A second crop of solid separated from the filtrate to provide additional end product: IR (KBr) 3420, 1785, 1708, 1620 cm$^{-1}$; mass spectrum m/z 579 (M$^+$ +H).

EXAMPLE 5

[6R-(6α,7β)]-3-[[[(5-ethyl-5,8-dihydro-8-oxo-1,3-dioxolo[4,5-q]quinolin-7-yl)carbonyl]oxy]methyl]-7-[(phenoxyacetyl) amino]-5-thia-1-azabicyclo[4.2.0]oct-2-ene-2-carboxylic acid 1,1-dimethylethyl ester A solution (1 mmol) of 5-ethyl-5,8-dihydro-8-oxo-1,3-dioxolo[4,5-q]quinoline-7-carboxylic acid sodium salt in 12 mL of DMF was dried by stirring under nitrogen with 1.50 g of 4A molecular sieves for 1 hour, and then combined with a solution of [6R-(6α,7β)]-3-(iodomethyl)-8-oxo-7-[(phenoxyacetyl)amino]-5-thia-1-azabicyclo[4.2.0]oct-2-ene-2-carboxylic acid 1,1-dimethylethylester in 6 mL of dry DMF and stirred for 5 hours. The mixture was concentrated to dryness. A solution of the residue in ethyl acetate or ethyl acetate/methylene chloride was washed with aqueous $NaHCO_3$ and brine, dried ($Na_2SO_4$) and concentrated to dryness. The residue was purified either by preparative TLC, or by flash chromatography using a 8:2 solvent mixture of ethyl acetate and methylene chloride.

EXAMPLE 6

[6R-(6α,7β)(Z)]-3-[[[(1-ethyl-1,4-dihydro-7-methyl-4-oxo-1,8-naphthyridin-3-yl)carbonyl]oxy]methyl]-7-[[(methoxyimino)[2-(triphenylmethyl)amino-4-thiazolyl]acetyl]amino]-8-oxo-5-thia-1-azabicyclo[4.2.0]oct-2-ene-2-carboxylic acid 1,1-dimethylethyl ester The reaction of Example 5 was repeated utilizing as reactants 1-ethyl-1,4-dihydro-7-methyl-4-oxo-1,8-naphthylridine-3-carboxylic acid sodium salt and [6R-(6α,7β)(Z)]-3-iodomethyl-7-[[(methoxyimino[2-(triphenylmethyl)amino-4-thiazolyl]acetyl]amino]-8-oxo-5-thia-1-azabicyclo[4.2.0]oct-2-ene-2-carboxylic acid 1,1-dimethylethyl ester. The residue in this Example was purified by flash chromatography using a 9:1 ethyl acetate/methylene chloride solvent mixture.

EXAMPLE 7

[6R-(6α,7β)(Z)]-3-[[[(5-ethyl-5,8-dihydro-8-oxo-1,3-dioxolo-[4,5-q]quinolin-7-yl)carbonyl]oxy]methyl]-7-[[(methoxy-imino)[2-(triphenylmethyl)amino-4-thiazolyl]acetyl]amino]-8-oxo-5-thia-1-azabicyclo[4.2.0]oct-2-ene-2-carboxylic acid 1,1-dimethylethyl ester The reaction of Example 5 was repeated utilizing as reactants 5-ethyl-5,8-dihydro-8-oxo-1,3-dioxolo[4,5-q]quinoline-7-carboxylic acid sodium salt and [6R-(6α,7β)(Z)]-3-iodomethyl-7-[[(methoxyimino)[2-(triphenylmethyl)amino-4-thiazolyl]acetyl]amino]-8-oxo-5-thia-1-azabicyclo[4.2.0]oct-2-ene-2-carboxylic acid 1,1-dimethylethyl ester. The residue in this Example was purified by flash chromatography using a 9:1 ethyl acetate/methylene chloride solvent mixture.

EXAMPLE 8

[6R-(6α,7β)]-3-[[[[1-Ethyl-6-fluoro-1,4-dihydro-7-(4-formyl-1-piperazinyl)-4-oxo-quinolin-yl]carbonyl]oxy]methyl]-8-oxo-7-[(phenoxyacetyl)amino]5-thia-1-azabicyclo-[4.2.0]oct-2-ene-2-carboxylic acid 1,1-dimethylethylester The reaction of Example 5 was repeated utilizing as reactants 1-ethyl-6-fluoro-1,4-dihydro-7-(4-formyl-1-piperazinyl)-4-oxo-quinoline-carboxylic acid monosodium salt and [6R-(6α,7β)]-3-(iodomethyl)-8-oxo-7-[(phenoxyacetyl)amino]-5-thia-1-azabicyclo[4.2.0]oct-2-ene-2-carboxylic acid 1,1-dimethylethyl ester. The residue in this Example was purified by flash chromatography using a 20:1 methylene chloride/methanol solvent mixture.

EXAMPLE 9

[6R-(6α,7β)-3-[[[(5-Ethyl-5,8-dihydro-8-oxo-1,3-dioxolo [4,5q]-quinolin-7-yl)carbonyl]oxy]methyl]-8-oxo-7-

[(phenoxyacetyl)-amino]-5-thia-1-azabicyclo[4.2.0]oct-2-ene-2-carboxylic acid sodium salt A solution of 3.00 g (4.52 mmol) of the end product of Example 5 in 15 mL of anisole was stirred at room temperature while 10.6 mL of trifluoroacetic acid was added. The mixture was stirred for 4 hours, and concentrated to dryness under reduced pressure. The residual oil was dissolved in methylene chloride, and water added. Sufficient NaHCO$_3$ was added to adjust the pH to 7.5. The mixture was stirred for 20 minutes before removing the aqueous phase. The addition of water and enough NaHCO$_3$ to adjust to pH 7.5 with stirring was repeated two more times. The three aqueous extracts were combined and freeze-dried. The residue was purified by C$_{18}$ reverse phase chromatography on a Waters Prep 500 A using 50% aqueous methanol to obtain, after evaporation and freeze drying, the title compound: 1R(KBr) 3410, 1765, 1692, 1635, 1528 cm$^{-1}$; mass spectrum m/z 630 (M$^+$+H), 652 (M$^+$+Na).

EXAMPLE 10

[6R-(6α,7β)(Z)]-7-[[(2-amino-4-thiazolyl)(methoxyimino) acetyl]amino]-3-[[[(1-ethyl-1,4-dihydro-7-methyl-4-oxo-1,8-naphthyridin-3-yl)carbonyl]oxy]methyl]-8-oxo-5-thia-1-azabicyclo-[4.2.0]oct-2-ene-2carboxylic acid sodium salt A suspension of 0.31 mmol of the end product of Example 6 in 0.66 mL of anisole was cooled to 0° C. under a nitrogen atmosphere, and 3.3 mL of trifluoroacetic acid was added. The resulting solution was kept at 0° C. for 18 hours, and then concentrated under reduced pressure at room temperature. Methylene chloride was added, and evaporation under reduced pressure was repeated. The residue was then triturated with ethyl acetate to obtain a solid, if possible, before conversion to the sodium salt. If it was not possible to obtain a solid, the residue was directly converted into the sodium salt. In either case, the solid or the residual oil was dissolved in 9 mL of methylene chloride and added dropwise at 0° to 3° C. to 9 mL of an aqueous NaHCO$_3$ solution containing sufficient NaHCO$_3$ to maintain a final pH of 7.2–7.4. The residue obtained after freeze-drying the aqueous phase was purified on a Waters analytical HPLC system using a Whatman M9 ODS-2 reverse phase column, and eluting with a water-methanol gradient (0–100% MeOH, 20 minutes). After evaporation and freeze drying, the end product was obtained: 1R (KBr) 3405, 3300, 3200, 1766, 1716, 1681, 1617, 1537 cm$^{-1}$.

EXAMPLE 11

[6R-(6α,7β)(Z)]-7-[[(2-Amino-4-thiazolyl)(methoxyimino) acetyl]amino]-3-[[[(5-ethyl-5,8-dihydro-8-oxo-1,3-dioxolo[4,5-q]quinolin-7-yl)carbonyl]oxy]methyl]-8-oxo-5-thia-1-azabicyclo-[4.2.0]oct-2-ene-2-carboxylic acid sodium salt Following the procedure of Example 10 but utilizing the end product of Example 7, there was obtained the title compound: 1R (KBr) 3400–3200, 1767, 1715, 1685, 1635, 1616, 1533 cm$^{-1}$; mass spectrum m/z 679 (M$^+$+H), 701 (M$^+$+Na).

EXAMPLE 12

[6R-(6α,7β)]-3-[[[[1-Ethyl-6-fluoro-1,4-dihydro-7-(4-formyl-1-piperazinyl)-4-oxo-quinolin-yl]carbonyl]oxy]methyl]-7-[(phenoxyacetyl)amino]-8-oxo-5-thia-1-azabicyclo[4.2.0]oct-2-ene-2-carboxylic acid sodium salt Following the procedure of Example 10 but utilizing the end product of Example 8, there was obtained the title compound: 1R (KBr) 3420, 1768; 1668, 1620 cm$^{-1}$; spectrum m/z 716 (M$^+$+H), 738 (M$^+$+Na).

EXAMPLE 13

[6R-(6α,7β)]-3-[[[(5-ethyl-5,8-dihydro-8-oxo-1,3-dioxolo[4,5-q]quinolin-7-yl)carbonyl]oxy]methyl]-8-oxo-7-[(2-thienylacetyl)-amino]-5-thia-1-azabicyclo[4.2.0]oct-2-ene-2-carboxylic acid 1,1-dimethylethyl ester Following the procedure of Example 5, but utilizing as reactants [6R-(6α,7β)]-3-(iodomethyl)-8-oxo-7-[(2-thienylacetyl)amino]-5-thia-1-azabicyclo[4.2.0]oct-2-ene-2-carboxylic acid 1,1-dimethylethyl ester and 5-ethyl-5,8-dihydro-7-oxo-1,3-dioxolo[4,5-q]quinolin-7-yl)carboxylic acid sodium salt, the title compound was obtained.

EXAMPLE 14

[6R-(6α,7β)]-3-[[[(5-Ethyl-5,8-dihydro-8-oxo-1,3-dioxolo[4,5-q]-quinolin-7-yl)carbonyl]oxy]methyl]-8-oxo-7-[(2-thienylacetyl)-amino]-5-thia-1-azabicyclo[4.2.0]oct-2-ene-2-carboxylic acid sodium salt Following the procedure of Example 10, but utilizing the end product of Example 13, the title compound was obtained: 1R (KBr) 3410, 1763, 1682, 1632, 1608 cm$^{-1}$; mass spectrum m/z 620 (M$^+$+H), 642 (M$^+$+Na).

EXAMPLE 15

[6R-(6α,7β)]-3-[[[[-Ethyl-6-fluoro-1,4-dihydro-7-(4-formyl-1-piperazinyl)-4-oxo-quinolin-yl]carbonyl]oxy]methyl]-7-[(2-thienylacetyl)amino]-8-oxo-5-thia-1-azabicyclo[4.2.0]oct-2-ene-2-carboxylic acid 1,1-dimethylethyl ester Following the procedure of Example 5, but utilizing as reactants [6R-(6α,6β)]-3-(iodomethyl)-8-oxo-7-[(2-thienylacetyl)amino]-5-thia-1-azabicyclo[4.2.0]oct-2-ene-2-carboxylic acid 1,1-dimethylethyl ester and 1-ethyl-6-fluoro-1,4-dihydro-7-(4-formyl-1-piperazinyl)-4-oxo-quinoline-carboxylic acid sodium salt, the title compound was obtained.

EXAMPLE 16

[6R-(6α,7β)]-3-[[[[1-Ethyl-6-fluoro-1,4-dihydro-7-(4-formyl-1-piperazinyl)-4-oxo-quinolin-yl]carbonyloxy]methyl]-7-[(2-thienylacetyl)amino]-8-oxo-5-thia-1-azabicyclo[4.2.0]oct-2-ene-2-carboxylic acid sodium salt Following the procedure of Example 10, but utilizing the end product of Example 15, the title compound was obtained: 1R (KBr) 3430, 1765, 1715, 1662, 1623 cm$^{-1}$; mass spectrum m/z 706 (M$^+$+H).

EXAMPLE 17

[6R-(6α,7β)(Z)]-3-[[[[1-Ethyl-6-fluoro-1,4-dihydro-7-(4-formyl-1-piperazinyl)-4-oxo-quinolin-yl]carbonyl]oxy]methyl]-7-[[(methoxyimino)[2-(triphenylmethyl)amino-4-thiazolyl]acetyl]-amino]-8-oxo-5-thia-1-azabicyclo[4.2.0]oct-2-ene-2-carboxylic acid 1,1-dimethylethyl ester.

Following the procedure of Example 5, but utilizing as reactants [6R-(6α,7β)(Z)]-3-(iodomethyl)-7-[[(methoxyimino)-[2-(triphenylmethyl)amino-4-thiazolyl]acetyl]amino]-8-oxo-5-thia-1-azabicyclo[4.2.0]oct-2-ene-2-carbocyclic acid 1,1-dimethylethyl ester and 1-ethyl-6-fluoro-1,4-dihydro-7-(4-formyl-1-piperazinyl)-4-oxo-quinoline-carboxylic acid sodium salt, the title product was obtained.

EXAMPLE 18

[6R-(6α,7β)(Z)]-7-[[(2-amino-4-thiazolyl)(methoxyimino)acetyl]-amino]-3-[[[[1-ethyl-6-fluoro-1,4-dihydro-7-(4-formyl-1-piperazinyl)-4-oxo-quinolin-3-yl]carbonyl]oxy]methyl]-8-oxo-5-thia-1-azabicyclo[4.2.0]oct-2-ene-2-carboxylic acid sodium salt Following the procedure of Example 10 but utilizing the end product of Example 17, the title compound was obtained: 1R (KBr) 3420, 1765, 1712, 1622 cm$^{-1}$; mass spectrum m/z 764 (M$^+$ +H).

EXAMPLE 19

[6R-(6α,7β)]-3-[[[[1-Ethyl-6-fluoro-1,4-dihydro-7-(1-pyrrolidinyl)-4-oxo-quinolin-yl]carbonyl]oxy]methyl]-7-[(phenoxyacetyl)amino]-8-oxo-5-thia-1-azabicyclo[4.2.0]oct-2-ene-2-carboxylic acid 1,1-dimethylethyl ester Following the procedure of Example 5, but utilizing as reactants [6R-(6α,7β)]-3-(iodomethyl)-8-oxo-7-[(phenoxyacetyl)-amino]-5-thia-1-azabicyclo[4.2.0]oct-2-ene-2-carboxylic acid 1,1-dimethylethyl ester and 1-ethyl-6-fluoro-1,4-dihydro-4-oxo-7-(1-pyrrolidinyl)-3-quinolinecarboxylic acid sodium salt, the title compound was obtained.

EXAMPLE 20

[6R-(6α,7β)]-3-[[[[1-Ethyl-6-fluoro-1,4-dihydro-7-(1-pyrrolidinyl)-4-oxo-quinolin-yl]carbonyl]oxy]methyl]-7-[(phenoxyacetyl)amino]-8-oxo-5-thia-1-azabicyclo[4.2.0]oct-2-ene-2-carboxylic acid sodium salt Following the procedure of Example 10, but utilizing the end product of Example 19, the title compound was obtained: 1R (KBr) 3410, 1770, 1695, 1628 cm$^{-1}$; mass spectrum m/z 673 (M$^+$ +H), 695 (M$^+$ +Na).

EXAMPLE 21

[6R-(6α,7β)](Z)-3-[[[[1-Ethyl-6-fluoro-1,4-dihydro-7-(1-pyrrolidinyl)-4-oxo-quinolin-yl]carbonyl]oxy]-methyl]-7-[[(methoxyimino)[2-(triphenylmethyl)amino-4-thiazolyl]acetyl]amino]-8-oxo-5-thia-1-azabicyclo[4.2.0]oct-2-ene-2-carboxylic acid 1,1-dimethylethyl ester Following the procedure of Example 5, but using as reactants [6R-(6α,7β)]-3-(iodomethyl)-7-[[(methoxyimino)[2-(triphenylmethyl)amino]-4-thiazolyl]acetyl]amino]-8-oxo-5-thia-1-azabicyclo[4.2.0]oct-2-ene-2-carboxylic acid 1,1-dimethylethyl ester and 1-ethyl-6-fluoro-1,4-dihydro-4-oxo-7-(1-pyrrolidioxyl)-3-quinoline carboxylic acid sodium salt, the title compound was obtained.

EXAMPLE 22

[6R-(6α,7β)(Z)]-7-[[(2-Amino-4-thiazolyl)(methoxyimino)acetyl]amino]-3-[[[[1-ethyl-6-fluoro-1,4-dihydro-7-(1-pyrrolidinyl)-4-oxo-quinolin-yl]carbonyl]oxy]-methyl]-8-oxo-5-thia-1-azabicyclo[4.2.0]oct-2-ene-2-carboxylic acid sodium salt Following the procedure of Example 10, but utilizing the end product of Example 21, the title compound was obtained: 1R (KBr) 3455, 3430, 1768, 1682, 1630 cm$^{-1}$; mass spectrum m/z 722 (M$^+$ +H).

EXAMPLE 23

[6R-(6α,7β)]-3-[[[[1-Ethyl-6-fluoro-1,4-dihydro-7-[4-(-1,1-dimethylethoxy)carbonyl-1-piperazinyl]-4-oxo-quinolin-yl]carbonyl]oxy]methyl]-8-oxo-7-[(phenoxyacetyl)amino]-5-thia-1-azabicyclo[4.2.0]oct-2-ene-2-carboxylic acid 1,1-dimethylethyl ester Following the procedure of Example 5, but using as reactants [6R-(6α,7β)]-3-iodomethyl-8-oxo-7-[(phenoxyacetyl)-amino]-5-thia-1-azabicyclo[4.2.0]oct-2-ene-2-carboxylic acid 1,1-dimethylethyl ester and 1-ethyl-6-fluoro-1,4-dihydro-7-[4-(1,1-dimethylethoxy)carbonyl-1-piperazinyl]-4-oxo-quinoline-carboxylic acid potassium salt, the title compound was obtained: 1R 3420, 1787, 1730, 1698, 1510 cm$^{-1}$; mass spectrum m/z 822 (M$^+$ +H).

EXAMPLE 24

[6R-(6α,7β)]-3-[[[[1-Ethyl-6-fluoro-1,4-dihydro-7-[4-(-1,1-dimethylethoxy)carbonyl-1-piperazinyl]-4-oxo-quinolin-yl]carbonyl]oxy]methyl]-8-oxo-7-[(phenoxyacetyl)amino]-5-thia-1-azabicyclo[4.2.0]oct-2-ene-2-carboxylic acid 2-propenyl ester Following the procedure of Example 5, but using as reactants [6R-(6α,7β)]-3-iodomethyl-8-oxo-7-[(phenoxyacetyl)-amino]-5-thia-1-azabicyclo[4.2.0]oct-2-ene-2-carboxylic acid 2-propenyl ester and 1-ethyl-6-fluoro-1,4-dihydro-7-[4-(1,1-dimethylethoxy)carbonyl-1-piperazinyl]-4-oxo-quinolino-carboxylic acid potassium salt, the title compound was obtained: 1R 3415, 3300, 1789, 1729, 1694, 1622 cm$^{-1}$; mass spectrum m/z 806 (M$^+$ +H).

EXAMPLE 25

[6R-(6α,7β)]-3-[[[[1-Ethyl-6-fluoro-1,4-dihydro-7-[4-(1-propenoxy)carbonyl-1-piperazinyl]-4-oxo-quinolin-yl]carbonyl]oxy]methyl]-8-oxo-7-[(phenoxyacetyl)amino]-5-thia-1-azabicyclo[4.2.0]oct-2-ene-2-carboxylic acid 2-propenyl ester Following the procedure of Example 5, but utilizing as reactants [6R-(6α,7β)]-3-iodomethyl-8-oxo-7-[(phenoxyacetyl)-amino]-5-thia-1-azabicyclo[4.2.0]oct-2-ene-2-carboxylic acid 2-propenyl ester and 1-ethyl-6-fluoro-1,4-dihydro-7-[4-(2-propenoxy)carbonyl-1-piperazinyl]-4-oxo-quinoline-3-carboxylic acid sodium salt, the title compound was obtained: 1R (KBr) 3410, 1789, 1725, 1699, 1622 cm$^{-1}$; mass spectrum m/z 790 (M$^+$ +H).

EXAMPLE 26

[6R-(6α,7β)]-3-[[[(5-Ethyl-5,8-dihydro-8-oxo-1,3-dioxolo[4,5-q]-quinolin-7-yl]carbonyl]oxy]methyl]-8-oxo-7-[(phenoxyacetyl)-amino]-8-oxo-5-thia-1-azabicyclo[4.2.0]oct-2-ene-2-carboxylic acid 2-propenyl ester Following the procedures of Example 5, but utilizing as reactants [6R-(6α,7β)]-3-iodomethyl-8-oxo-7-[(phenoxyacetyl)-amino]-5-thia-1-azabicyclo[4.2.0]oct-2-ene-2-carboxylic acid 2-propenyl ester and 5-ethyl-5,8-dihydro-8-oxo-1,3-dioxalo[4,5-g]quinoline-7-carboxylic acid sodium salt, the title compound was obtained.

EXAMPLE 27

Alternate synthesis of [6R-(6α,7β)]-3-[[[(5-ethyl-5,8-dihydro-8-oxo-1,3-dioxolo[4,5-q]quinolin-7-yl]carbonyl]oxy]methyl]-8-oxo-7-[(phenoxyacetyl)amino]-5-thia-1-azabicyclo[4.2.0]oct-2-ene-2-carboxylic acid sodium salt To a stirred solution of 337 mg of the end product of Example 26, 0.03 mL of triethyl phosphite, 5.6 mg of palladium II acetate, 3.9 mL of ethyl acetate, and 5.6 mL of methylene chloride was added dropwise 1.68 mL of a 0.5 molar solution of sodium 2-ethylhexanoate in ethyl acetate, over a 15 minute period. The mixture was stirred for 30 minutes; 11 mL of acetone was added, and stirring continued for 10 minutes. The product was filtered, washed with ether, and air dried. After purification by $C_{18}$ reverse phase HPLC, the title compound was obtained. This product was identical in its spectral properties to the product of Example 9.

EXAMPLE 28

[6R-(6α,7β)]-3-[[[[1-Ethyl-6-fluoro-1,4-dihydro-7-(4-thiomorpholinyl)-4-oxo-quinolin-yl]carbonyl]oxy]methyl]-8-oxo-7-](phenoxyacetyl)amino]-5-thia-1-azabicyclo[4.2.0]oct-2-ene-2-carboxylic acid sodium salt A solution of 0.187 g of 1-ethyl-6-fluoro-1,4-dihydro-4-oxo-7-(4-thiomorpholinyl)-3-quinoline-carboxylic acid potassium salt in 8 mL of DMF was stirred with 4A molecular sieves for one hour. Then a solution of 0.257 g of [6R-(6α,7β)]-3-(iodomethyl)-8-oxo-7-[(phenoxyacetyl)amino]-5-thia-1-azabicyclo[4.2.0]oct-2-ene-2-carboxylic acid 2-propenyl ester in 8 mL of DMF was added, and the mixture stirred for 5 hours. The mixture was concentrated under reduced pressure. A solution of the residue in ethyl acetate was washed with aqueous $NaHCO_3$ and with brine, dried ($Na_2SO_4$), and concentrated under reduced pressure. The residue was purified by preparative TLC to obtain 0.109 g of intermediate allyl ester.

To a solution of 63.5 mg of allyl ester in 1.1 mL of methylene chloride and 0.75 mL of ethyl acetate were added 5.1 μl of triethyl phosphate, 1 mg of palladium (II) acetate, and 0.28 mL of a 0.5M sodium 2-ethylhexanoate solution in ethyl acetate. The mixture was stirred for one hour, before adding 2 mL of acetones and concentrating to dryness under reduced pressure. The residue was triturated with ether to obtain a solid. Purification by reverse phase HPLC provided the title compound: 1R (KBr) 3420, 1768, 1695, 1622 cm$^{-1}$; mass spectrum m/z 705 (M$^+$+H), 727 (M$^+$+Na).

EXAMPLE 29

[6R-(6α,7β)]-3-[[[(1-Ethyl-6-fluoro-1,4-dihydro-4-oxo-7-(1H-pyrrol-1-yl)quinolin-3-yl]carbonyl]oxy]methyl]-8-oxo-7-[(phenoxyacetyl)amino]-5-thia-1-azabicyclo[4.2.0]oct-2-ene-2-carboxylic acid sodium salt A solution of 0.845 g of 1-ethyl-6-fluoro-1,4-dihydro-4-oxo-7-(1H-pyrrol-1-yl)-3-quinolinecarboxylic acid potassium salt in 30 mL of DMF was stirred for one hour with 4A molecular sieves; 1.54 g of [6R-(6α,7β)]-3-iodomethyl-8-oxo-7-[(phenoxyacetyl)amino]-5-thia-1-azabicyclo[4.2.0]oct-2-ene-2-carboxylic acid 2-propenyl ester was added and the mixture stirred for 2.5 hours. The mixture was concentrated under reduced pressure. Ethyl acetate was added, and the mixture washed with aqueous $NaHCO_3$ and brine. After drying ($Na_2SO_4$) the ethyl acetate was evaporated under reduced pressure, and the residue purified by flash chromatography to obtain the intermediate allyl ester.

To a solution of 69 mg of allyl ester in 1 mL of methylene chloride were added 0.3 mg of palladium (II) acetate, 1 μL of triethylphosphite, 0.2 mL of 0.5M sodium 2-ethylhexanoate solution in ethyl acetate, and 0.3 mL of ethyl acetate. After stirring for 30 minutes, the mixture was concentrated under reduced pressure. Trituration of the residue with ether gave a solid. Purification by reverse phase HPLC provided the title compound: 1R (KBr) 3420, 1765, 1695, 1620 cm$^{-1}$; mass spectrum m/z 669 (M$^+$+H), 691 (M$^+$+Na).

EXAMPLE 30

[6R-(6α,7β)]-3-[[[[5-(4-fluorophenyl)-5,8-dihydro-8-oxo-1,3-dioxolo[4,5-g]quinolin-7-yl]carbonyl]oxy]methyl]-8-oxo-7-[(phenoxyacetyl)amino]-5-thia-1-azabicyclo[4.2.0]oct-2-ene-2-carboxylic acid sodium salt A solution of 0.183 g of 5-(4-fluorophenyl)-5,8-dihydro-8-oxo-1,3-dioxolo[4,5-g]quinoline-7-carboxylic acid potassium salt in 8 mL of DMF was stirred for one hour with 4A molecular sieves. A solution of 0.308 g of [6R-(6α, 7β)]-3-iodomethyl-8-oxo-7-[(phenoxyacetyl)amino]-5-thia-1-azabicyclo[4.2.0]oct-2-ene-2-carboxylic acid 2-propenyl ester was added, and the mixture stirred for 5 hours. The mixture was concentrated under reduced pressure, and ethyl acetate added to the residue. The mixture was washed with aqueous $NaHCO_3$ and brine. After drying ($Na_2SO_4$) the ethyl acetate was concentrated under reduced pressure and the residue purified by preparative TLC to obtain 0.129 g of intermediate allyl ester.

To a solution of 0.122 g of allyl ester in 2.1 mL of methylene chloride and 1.5 mL of ethyl acetate were added 9.9 μL of triethyl phosphite, 1.94 mg of palladium (II) acetate, and 0.51 mL of 0.5M sodium 2-ethylhexanoate solution in ethyl acetate. The mixture was stirred for one hour, diluted with acetone, and concentrated under reduced pressure. The residue was triturated with ether to obtain 0.128 g of solid. After purification by reverse phase HPLC, the title compound (28.6 mg) was obtained: 1R (KBr) 3420, 1765, 1695, 1632 cm$^{-1}$; mass spectrum m/z 696 (M$^+$+H), 718 (M$^+$+Na).

EXAMPLE 31

[6R(6α,7β)(Z)]-7-[[(2-Amino-4-thiazolyl) (methoxyimino) acetyl[amino[-3-[[[[1-ethyl-6-fluoro-1,4-dihydro-7-(4-thiomorpholinyl)-4-oxo-quinolin-yl]carbonyl]oxy]methyl]-8-oxo-5-thia-1-azabicyclo[4.2.0]oct-2-ene-2-carboxylic acid sodium salt A solution of 0.374 g of 1-ethyl-6-fluoro-1,4-dihydro-4-oxo-7-(4-thiomorpholinyl)-3-quinolinecarboxylic acid potassium salt in 16 mL of DMF was stirred for 1 hour with 1.5 g of 4A molecular sieves. A solution of 1.07 g of [6R-(6α,7β)]-3-iodomethyl-7-[[(methoxyimino)[(2-triphenylmethyl)amino-4-thiazolyl]acetyl]amino]-8-oxo-5-thia-1-azabicyclo[4.2.0]oct-2-ene-2-carboxylic acid 1,1-dimethylethyl ester in 16 mL of DMF was added and the mixture stirred for 5 hours. The mixture was concentrated under reduced pressure, the residue taken up in ethyl acetate, and the mixture washed with aqueous $NaHCO_3$ and brine. After drying ($Na_2SO_4$), the ethyl acetate solution was concentrated under reduced pressure. The residue was purified by flash chromatography to obtain 0.365 g of intermediate t-butyl ester.

The t-butyl ester (0.103 g) was dissolved in a mixture of 0.21 mL of anisole and 1.06 mL of trifluoroacetic acid and kept at 0° C. for 18 hours. The mixture was concentrated under reduced pressure, and the residue dissolved in methylene chloride. Water and $NaHCO_3$ were added to a pH of 7.5. The aqueous phase was freeze-dried. The title compound was obtained by purification of the residue by reverse-phase HPLC: 1R (KBr) 3410, 1768, 1715, 1682, 1622 cm$^{-1}$; mass spectrum m/z 754 (M$^+$+H).

EXAMPLE 32

[6R-[6α,7β(Z)]]-7-[[(2-Amino-4-thiazolyl-(methoxyimino) acetyl]amino]-3-[[[[6,8-difluoro-1-(2-fluoroethyl)-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid monosodium salt dihydrate A solution of 10 g of [6R-(6α,7β]-3-(iodomethyl)-7-[[(methoxyimino)[2-(triphenylmethyl)amino]-4-thiazolylacetyl]amino]-8-oxo-5-thia-1-azabicyclo[4.2.0]oct-2-ene-2-carboxylic acid 1,1-dimethylethyl ester in 40 mL of DMF was added to a suspension of 5 g of 6,8-difluoro-1-(2-fluoroethyl)-1,4-dihydro-7-(4-methyl-1-piperazinyl)-4-oxo-3-quinolinecarboxylic acid potassium salt in 40 mL of DMF over a five minute period. The mixture was stirred for two hours, and then concentrated under reduced pressure. The residue was partitioned between ethyl acetate and aqueous sodium bicarbonate. The organic phase was washed with aqueous sodium bicarbonate and brine, dried (MgSO$_4$) and solid was dissolved in 100 mL of 1:4 methanol-chloroform, and with ice cooling, 100 mL of water and 35 mL of 5% aqueous sodium bicarbonate were added, adjusting the pH to 7.8. The gum which separated during this operation was dissolved in 10 mL of DMF; 20 mL of chloroform was added, followed by water and aqueous bicarbonate to pH 7.8. The combined aqueous extracts containing the product were washed with chloroform, and purified by reverse phase chromatography on C$_{18}$ packing (Waters Associates), using a water-acetonitrile gradient. The appropriate fractions were concentrated under reduced pressure and lyophilized to yield 0.65 g of the title compound: mass spectrum m/z 787 (M$^+$ + H).

Following the procedures set forth in the Examples, there can be prepared the following compounds:

[6R-[6α,7β(Z)]]-7-[[(2-Amino-4-thiazolyl) (methoxyimino) acetyl]amino]-3-[[[[1-ethyl-6-fluoro-1,4-dihydro-7-(1-piperazinyl)-3-quinolinyl]carbonyl]oxy]methyl]-8-oxo-5-thia-1-azabicyclo[4.2.0]oct-2-ene-2-carboxylic acid

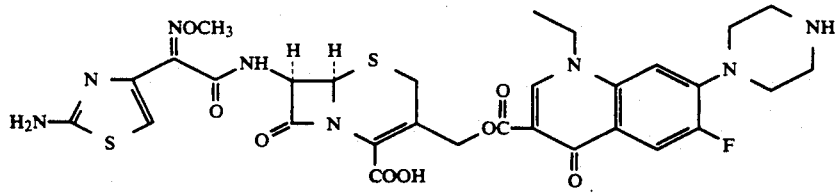

concentrated to give 16.8 g of brown foam. Purification by flash chromatography on 500 g of silica gel (230–400 mesh) using methanol-chloroform (gradient from 0 to 8% methanol) provided 5.42 g of intermediate ester.

[6R-(6α,7β)]-3-[[[[1-ethyl-6-fluoro-1,4-dihydro-4-oxo-7-(1-piperazinyl)-3-quinolinyl]carbonyl]oxy]methyl]-8-oxo-7-[(phenoxyacetyl)amino]-5-thia-1-azabicyclo[4.2.0]oct-2-ene-2-carboxylic acid

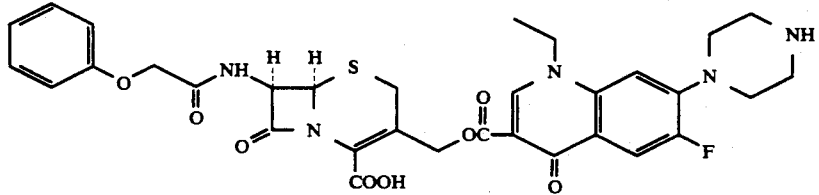

To a solution of 2.30 g of this intermediate in 25 mL of methylene chloride at 0° C. were added 2 mL of anisole, 0.2 mL of 1,2-ethanedithiol, and 25 mL of trifluoroacetic acid. The mixture was stirred at 0° C. for 3.5 hours, and then concentrated under reduced pressure,

[6R-(6α,7β)]-3-[[[[6,8-difluoro-1-(2-fluoroethyl)-1,4-dihydro-7-(4-methyl-1-piperazinyl)-4-oxo-3-quinolinyl]carbonyl]oxy]methyl]-8-oxo-7-[(phenoxyacetyl)amino]-5-thia-1-azabicyclo[4.2.0]oct-2-ene-2-carboxylic acid

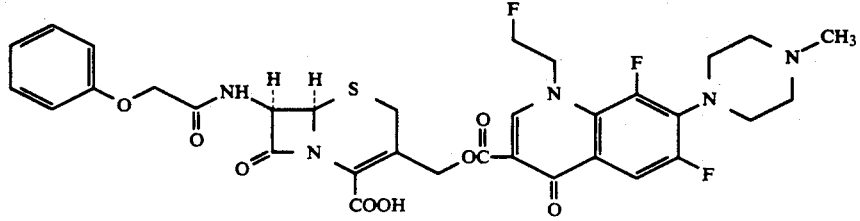

at 0° C. Methylene chloride was added to the residue, and the evaporation repeated. To the residue was added 5 mL of cold ethyl acetate, followed by 25 mL of ether, precipitating a solid. After filtering, washing with ether, and air-drying, 3.1 g of tan solid was obtained. This

[6R-[6α,7β(Z)]]-7-[[(2-amino-4-thiazolyl) (methoxyimino) acetyl]amino]-3-[[[[1-ethyl-6-fluoro-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid

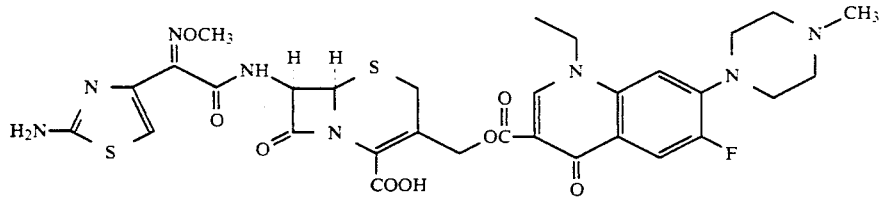

[6R-(6α,7β)]-3-[[[[1-ethyl-6-fluoro-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid

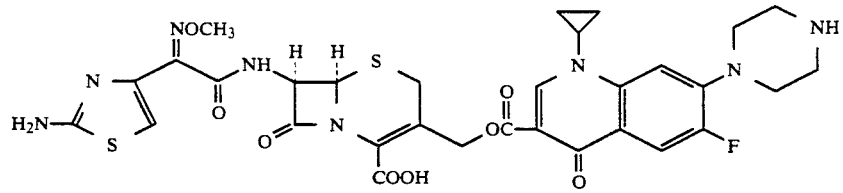

bonyl]oxy]methyl]-3-oxo-7-[(phenoxyacetyl)amino]-5-thia-[-azabicyclo[4.2.0]oct-2-ene-carboxylic acid

[6R-(6α,7β)]-7-[(cyanoacetyl)amino]-3-[[[[6,8-difluoro-1-(2-fluoroethyl)-1,4-dihydro-7-(4-methyl-1-

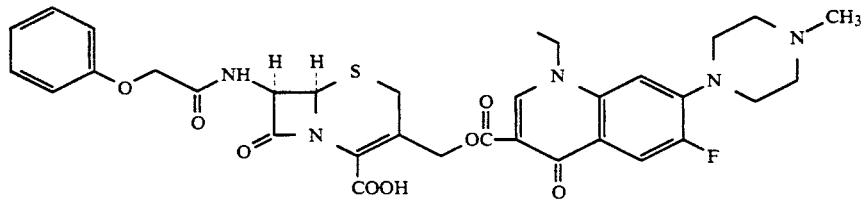

[6R-[6α,7β)]-3-[[[[1-cyclopropyl-6-fluoro-1,4-dihydro-7-(1-piperazinyl)-4-oxo-3-quinolinyl]carbonyl]oxy]methyl]8-oxo-7-[(phenoxyacetyl)amino]-5-thia-1-azabicyclo[4.2.0]oct-2-ene-2-carboxylic acid piperazinyl)-4-oxo-3-quinolinyl]carbonyl]oxy]methyl]-8-oxo-5-thia-1-azabicyclo[4.2.0]oct-2-ene-2-carboxylic acid

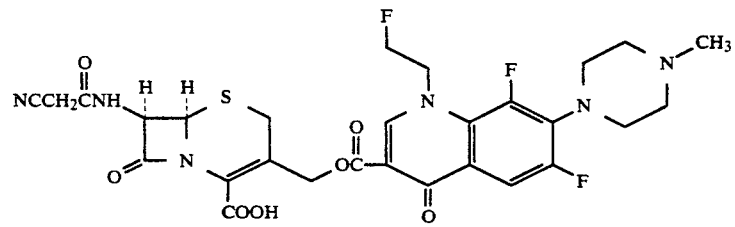

[6R-(6α,7β)]-7-(formylamino)-3-[[[[6,8-difluoro-1-(2-f-

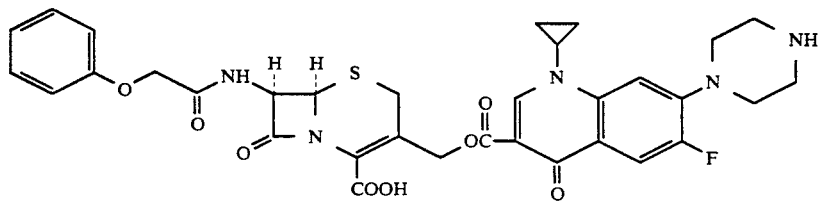

[6R-[6α,7β(Z)]]-7-[[(2-amino-4-thiazolyl)methoxyimino]acetyl]amino]-3-[[[[1-cyclopropyl-6-fluoro-1,4-dihydro-4-oxo-7-(1-piperazinyl)-3-quinolinyl]carluoroethyl)-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid

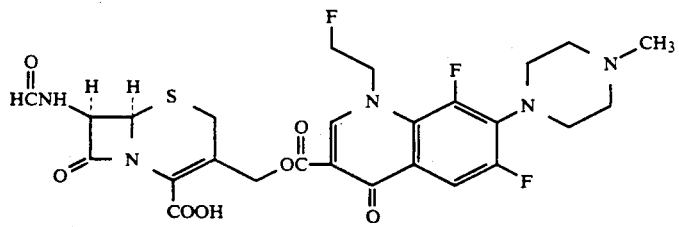

[6R-(6α,7β)]-7-[[[[(4-ethyl-2,3-dioxo-1-piperazinyl)carbonyl]amino]phenylacetyl]amino]-3-[[[[6,8-difluoro-1-(2-fluoroethyl)-1,4-dihydro-4-oxo-3-quinolinyl]carbonyl]oxy]methyl]-8-oxo-5-thia-1-azabicyclo[4.2.0]oct-2-ene-2-carboxylic acid

[6R-[6α,7β(Z)]]-7-[[[(2-amino-4-thiazolyl)(carboxymethoxy)imino]acetyl]amino]-3-[[[[6,8-difluoro-1-(2-fluoroethyl)-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-car-

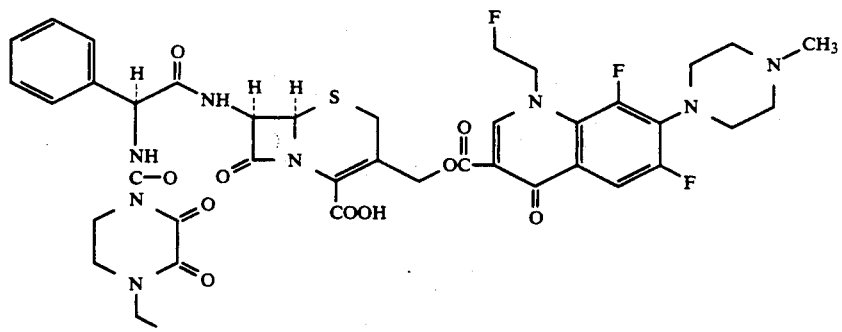

[6R-[6α,7β(Z)]]-7-[[(2-amino-4-thiazolyl)[[(1-carboxy boxylic acid

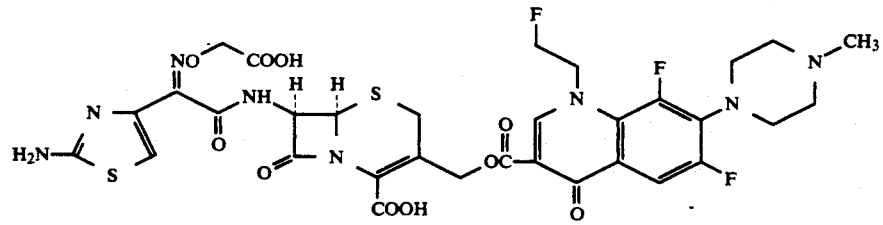

-1-methyl)ethoxy]imino]acetyl]amino]-3-[[[[6,8-difluoro-1-(2-fluoroethyl)-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid

[6R-(6α,6β)]-3-[[[[6,8-difluoro-1-(2-fluoromethyl)-1,4-dihydro-7-(4-methyl-1-piperazinyl)-4-oxo-3-quinolinyl]carbonyl]oxy]methyl]-8-oxo-7-[(phenylacetyl)amino]-5-thia-1-azabicyclo[4.2.0]oct-2-ene-2-carboxylic acid

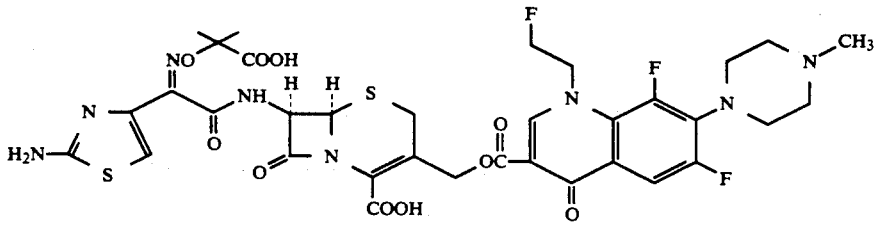

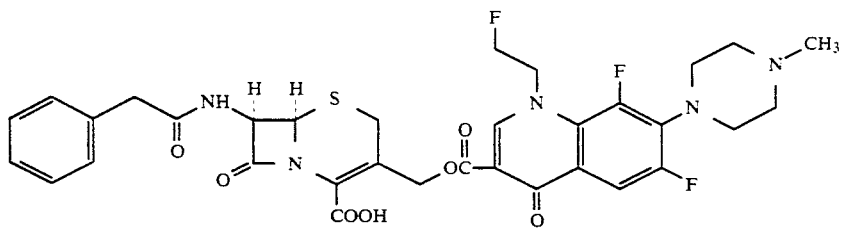

[6R-(6α,7β)]-3-[[[[6,8-difluoro-1-(2-fluoroethyl-1,4-dihydro-7-(4-methyl-1-piperazinyl)-4-oxo-3-quinolinyl]carbonyl]oxy]methyl]-8-oxo-7-[(2-thienylacetyl)amino]-5-thia-1-azabicyclo[4.2.0]oct-2-ene-2-carboxylic acid

[6R-(6α,7β)]-3-[[[[6-fluoro-1-(4-fluorophenyl)-1,4-dihydro-7-(4-methyl-1-piperazinyl)-4-oxo-3-quinolinyl]carbonyl]oxy]methyl]-8-oxo-7-[(phenoxyacetyl)amino]-5-thia-1-azabicyclo[4.2.0]oct-2-ene-2-carboxylic acid

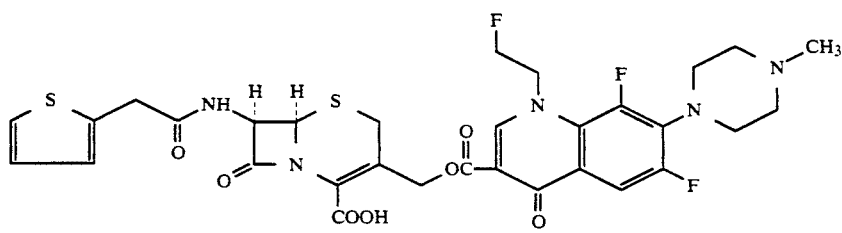

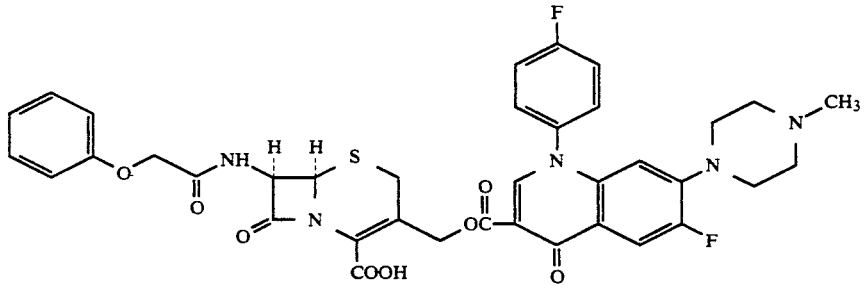

[6R-[6α,7β(Z)]]-7-[[(2-amino-4-thiazolyl)(methoxyimino)acetyl]amino]-3-[[[[6,8-difluoro-1-(4-fluorophenyl)-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid

[6R-(6α,7β)]-3-[[[[9-fluoro-3,7-dihydro-3-methyl-10-(4-methyl-1-piperazinyl)-7-oxo-2H-pyrido[1,2,3-de]-1,4-benzoxazin-6-yl]carbonyl]oxy]methyl]-8-oxo-7-[(phenoxyacetyl)amino]-5-thia-1-azabicyclo[4.2.0]oct-2-ene-2-carboxylic acid

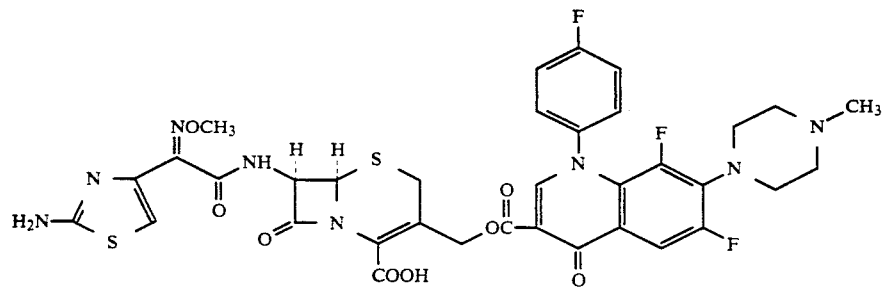

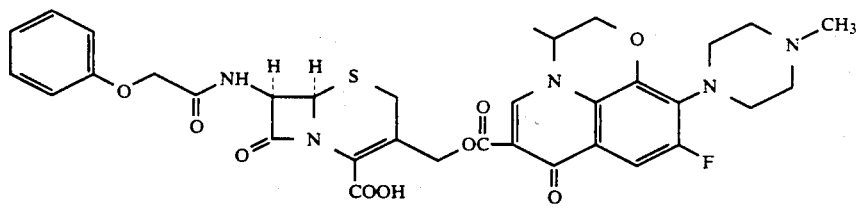

[6R-[6α,7β(Z)]]-7-[[[(2-amino-4-thiazolyl)methoxyimino]acetyl]amino]-3-[[[[9-fluoro-3,7-dihydro-3-methyl-10-(4-methyl-1-piperazinyl)-7-oxo-2H-pyrido[1,2,3-de]-1,4-benzoxazin-6-yl]carbonyl]oxy]methyl]-8-oxo-5-thia-1-azabicyclo[4.2.0]oct-2-ene-2-carboxylic acid

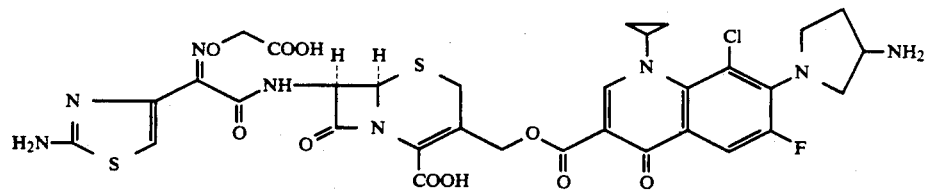

[6R-[6α,7β(Z)]]-3-[[[[7-(3-amino-1-pyrrolidinyl)-8-chloro-1-cyclopropyl-6-fluoro-1,4-dihydro-4-oxo-3-quinolinyl]carbonyl]oxy]methyl]-7-[[(2-amino-4-thiazolyl)[(carboxymethoxy)imino]acetyl]amino]-8-oxo-5-thia-1-azabicyclo[4.2.0]oct-2-ene-2-carboxylic acid

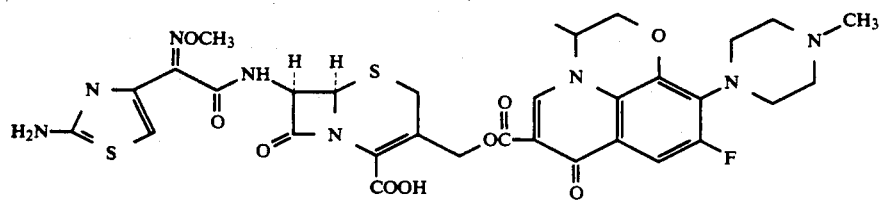

[6R-(6α,7β)]-α[[[2-carboxy-3-[[[[6,8-difluoro-1-(2-fluoroethyl)-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-en-7-yl]amino]carbonyl]benzeneacetic acid

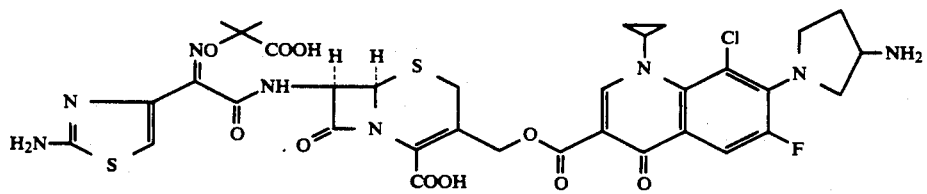

[6R-[6α,7β(Z)]]-7-[[(2-amino-4-thiazolyl)[(1-carboxy-1-methylethoxy)imino]acetyl]amino]-8-oxo-5-thia-1-azabicyclo[4.2.0]oct-2-ene-2-carboxylic acid

[6R-[6α,7β(Z)]]-3-[[[[7-(3-amino-1-pyrrolidinyl)-8-chloro-1-cyclopropyl-6-fluoro-1,4-dihydro-4-oxo-3-

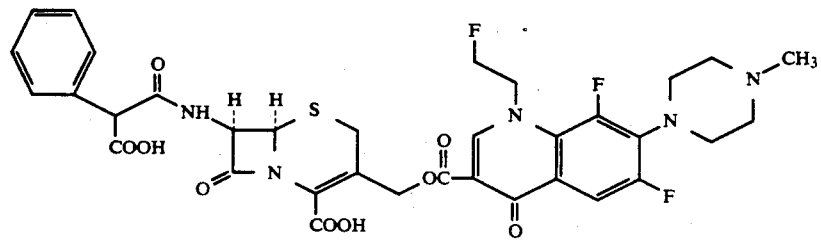

[6R-[6α,7β(Z)]]-3-[[[[7-(3-amino-1-pyrrolidinyl)-8-chloro-1-cyclopropyl-6-fluoro-1,4-dihydro-4-oxo-3-quinolinyl]carbonyl]oxy]methyl]-7-[[(2-amino-4-thiazolyl)(methoxyimino)acetyl]amino]-8-oxo-5-thia-1-azabicyclo[4.2.0]oct-2-ene-2-carboxylic acid

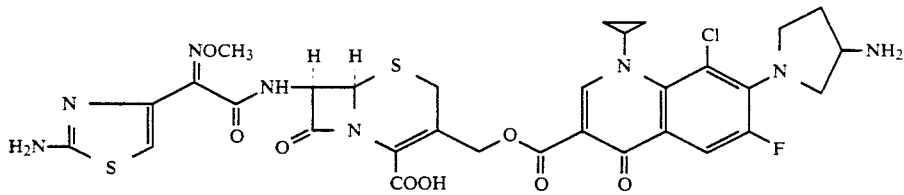

What is claimed:

1. A compound of the formula

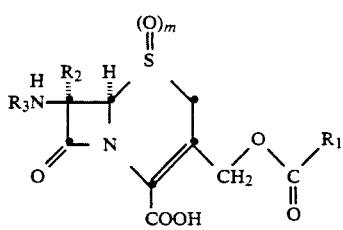

wherein R, is quinolonyl or azaquinolonyl group which can be unsubstituted or substituted; group $R_2$ is selected from the group consisting of hydrogen, lower alkoxy, amino, lower alkylthio and amido; $R_3$ is an acyl group derived from a carboxylic acid; and m is 0, 1, 2, or a readily hydrolyzable ester or salt of the compound, or hydrate of the compound, ester or salt.

2. A compound as in claim 1 wherein m is zero and $R_2$ is hydrogen.

3. A compound as in claim 2 wherein $R_1$ is

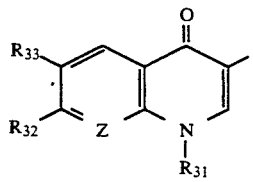

wherein Z represents

or N, $R_{30}$ represents hydrogen, chloro, bromo or fluoro, $R_{31}$ represents hydrogen, lower alkyl, lower alkenyl, $C_3$-$C_7$ cycloalkyl, chloro-, bromo- or fluoroloweralkyl or chloro-, bromo- or fluorophenyl, $R_{30}$ and $R_{31}$ when taken together represents lower alkylene of 3-5 carbon atoms, a lower alkylene mono-oxy group of 2-4 carbon atoms or a lower alkylene dioxy group having 1-2 carbon atoms, $R_{32}$ represents hydrogen, chlorine, bromine, fluorine, lower alkyl, or a 5- or 6-membered heterocyclic ring containing one to three heteroatoms selected from the group consisting of O, N and S, the remainder of the ring atoms being carbon, the ring being optionally substituted with at least one substituent selected from the group consisting of lower alkyl, lower alkoxy, halogen, halogen substituted alkyl, aminomethyl, ethylaminomethyl, amino, mercapto, hydroxyl, carbamoyl, and carboxyl, $R_{33}$ represents hydrogen chlorine, bromine or fluorine, and $R_{32}$ and $R_{33}$ when taken together represents a $C_1$-$C_4$ lower alkylene dioxy group.

4. A compound as in claim 3 wherein Z is

wherein $R_{30}$ is hydrogen, chlorine, bromine or fluorine, $R_{31}$ is lower alkyl, chloro-, bromo- or fluoroloweralkyl or $C_3$-$C_7$ cycloalkyl, $R_{32}$ is lower alkyl, piperazinyl or lower alkylpiperazinyl and $R_{33}$ is hydrogen, chlorine, bromine or fluorine.

5. A compound as in claim 4 wherein $R_{30}$ is hydrogen or fluorine, $R_{31}$ is ethyl, fluoroethyl or cyclopropyl, $R_{32}$ is piperazinyl or 4-methylpiperazinyl, and $R_{33}$ is hydrogen or fluorine.

6. The compound of claim 1 wherein the acyl group is a carbocylic aromatic group of the formula

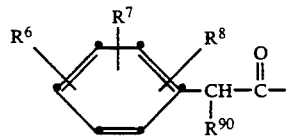

wherein $R^{90}$ is selected from the group consisting of amino, acylamino, hydroxyl, a carboxyl salt, benzyloxycarbonyl, formyloxy or azido; $R^6$, $R^7$ and $R^8$ is selected from the group consisting of hydrogen, halogen, hydroxyl, nitro, amino, cyano, trifluoromethyl, $C_1$-$C_4$ alkyl, $C_1$ to $C_4$ alkoxy and aminomethyl.

7. The compound of claim 6 wherein $R^6$, $R^7$, $R^8$ are hydrogen and $R^{90}$ is hydrogen or hydroxy.

8. The compound of claim 1 wherein the acyl group is a group of the formula

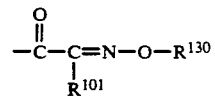

wherein $R^{101}$ is a unsubstituted or substituted 5, 6-or 7-membered heterocyelic ring containing 1, 2, 3 or 4 hetero atoms independently selected from the group consisting of nitrogen, oxygen and sulfur atoms, the remainder of the ring atoms being carbon, wherein the heterocyclic ring is substituted by halogen, hydroxy, nitro, amino, cyano, trifluoromethyl, $C_1$ to $C_4$ alkyl or $C_1$ to $C_4$ alkoxy and $R^{130}$ is hydrogen, lower alkyl, $C_3$-$C_7$ cycloalkyl and substituted lower alkyl wherein the lower alkyl is substituted with one or more halogen, cyano, nitro, amino, mercapto, lower alkylthio, carboxyl (including salts thereof), amido, lower alkoxycarbonyl, phenylmethoxycarbonyl, diphenylmethoxycarbonyl, hydroxyalkoxyphosphinyl, dihydroxyphosphinyl, hydroxy (phenylmethoxy)phosphinyl, diloweralkoxyphosphinyl, carboxy lower alkyl or carboxyl-3,7-cycloalkyl.

9. A compound as in claim 1 wherein the acyl group $R_3$ is of the formula

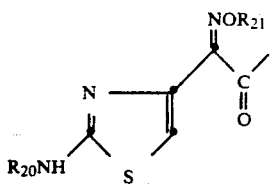

wherein
$R_{20}$ is hydrogen or an amino protecting group $R_{21}$ is hydrogen, lower alkyl or a group of the formula

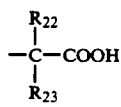

wherein
$R_{22}$ and $R_{23}$ are selected from the group consisting of hydrogen, lower alkyl or taken together with the carbon atom to which they are attached form a 3–7 carbocyclic ring.

10. A compound as in claim 9 wherein $R_{20}$ is hydrogen, $R_{21}$ is methyl or

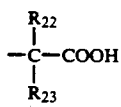

wherein $R_{22}$ and $R_{23}$ are selected from the group consisting of hydrogen and methyl.

11. A compound as in claim 1 of the formula

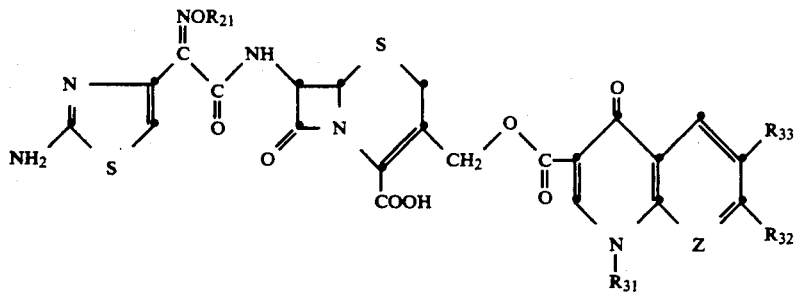

wherein $R_{21}$ is hydrogen, lower alkyl or a group of the formula

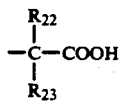

wherein $R_{22}$ and $R_{23}$ are selected from the group consisting of hydrogen and lower alkyl or $R_{22}$ and $R_{23}$ taken together with the carbon atom to which they are attached form a 3–7 carbocyclic ring, Z represents

or N; $R_{30}$ represents hydrogen or halogen; $R_{31}$ is hydrogen, lower alkyl, lower alkenyl, $C_3$–$C_7$ cycloalkyl, halo lower alkyl, or mono, di and tri-halophenyl; $R_{30}$ and $R_{31}$ when taken together represent lower alkylene of 3–5 carbon atoms, a lower alkylene mono-oxy group of 2–4 carbon atoms or a lower alkylene dioxy group having 1–2 carbon atoms; $R_{32}$ represents hydrogen, halogen, lower alkyl, a 5- or 6-membered heterocyclic ring containing one or two heteroatoms selected from the group consisting of O, N and S, the remainder of the ring atoms being carbon, $R_{33}$ represents hydrogen and halogen, and $R_{32}$ and $R_{33}$ when taken together represent a $C_1$–$C_4$ lower alkylene dioxy group.

12. A compound as in claim 11 wherein $R_{21}$ is methyl or the group of the formula

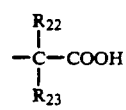

wherein $R_{22}$ and $R_{23}$ are hydrogen or methyl. Z is

wherein $R_{30}$ is hydrogen and halogen, $R_{31}$ is lower alkyl, halo-lower alkyl or $C_3$–$C_7$ cycloalkyl. $R_{32}$ is lower alkyl, piperazinyl or lower alkylpiperazinyl and $R_{33}$ is hydrogen or halogen.

13. A compound as in claim 12 wherein $R_{30}$ is hydrogen or fluorine, $R_{31}$ is ethyl, fluoroethyl or cyclopropyl, $R_{32}$ is methyl, 4-methyl piperazinyl or piperazinyl and $R_{33}$ is hydrogen or fluorine.

14. A compound as in claim 1 of the formula [6R-(6α,7β)]-3-[[[(1-Ethyl-1,4-dihydro-7-methyl-4-oxo-1,8-naphthyridin-3-yl) carbonyl]oxy]methyl]-8-oxo-7-[(phenoxyacetyl) amino]-5-thia-1-azabicyclo[4.2.0]oct-2-ene-2-carboxylic acid hydrate.

15. A compound as in claim 1 of the formula [6R-(6α,7β)]-3-[[[(5-Ethyl-5,8-dihydro-8-oxo-1,3-dioxolo[4,5-g]quinolin-7-yl)carbonyl]oxy]methyl]-8-oxo-7-[(phenoxyacetyl)amino]-5-thia-1-azabicyclo[4.2.0]oct-2-ene-2-carboxylic acid monosodium salt.

16. A compound as in claim 1 of the formula [6R-(6α,7β) (Z)]-[[(Z)]-7-Amino-4-thiazolyl)(methoxyimino)acetyl]amino]-3-[[[(1-ethyl-1,4-dihydro-7-methyl-4-oxo-1,8naphthyridin-3-yl)carbonyl]oxy]methyl]-8-oxo-5-thia-1-azabicyclo[4.2.0]oct-2-ene-2-carboxylic acid sodium salt.

17. A compound as in claim 1 of the formula [6R-(6α,7β) (Z)]-[[(2)]-7-Amino-4-thiazolyl)(methoxyimino)acetyl]amino]-3-[[[(5-ethyl-5,8-dihydro-8-oxo-1,3-dioxolo[4,5-g]quinolin-7-yl)carbonyl]oxy]methyl]-8- oxo-5-thia-1-azabicyclo[4.2.0]oct-2-ene-2-carboxylic acid sodium salt.

18. A compound as in claim 1 of the formula [6 R-(6α,7β)]-3-[[[[1-Ethyl-6-fluoro-1,4-dihydro-7-(4-formyl-1-piperazinyl)-4-oxo-quinolin-3-yl]carbonyl]oxy]methyl]-8-oxo-7-[(phenoxyacetyl)amino]-5-thia-1-azabicyclo[4.2.0]oct-2-ene-2-carboxylic acid sodium salt.

19. A compound as in claim 1 of the formula [6R-(6α,7β)]-3-[[[(5-Ethyl-5,8-dihydro-8-oxo-1,3-dioxolo[4,5-g]quinolin-7-yl)carbonyl]oxy]methyl]-8-oxo-7-[(2-thienylacetyl)amino]-5-thia-1-azabicyclo[4.2.0]oct-2-ene-2-carboxylic acid sodium salt.

20. A compound as in claim 1 of the formula [6R-(6α,7β)]-3-[[[[1-Ethyl-6-fluoro-1,4-dihydro-7-(4-formyl-1-piperazinyl)-4-oxoquinolin-3-yl]carbonyl]oxy]methyl]-7-[(2-thienylacetyl)amino]-5-thia-1-azabicyclo[4.2.0]oct-2-ene-2-carboxylic acid sodium salt.

21. A compound as in claim 1 of the formula [6R-(6α,7β)]-3-[[[[1-Ethyl-6-fluoro-1,4-dihydro-7-(1-pyrrolidinyl)-4-oxo-quinolin-3-yl]carbonyl]oxy]methyl]-8-oxo-7-[(phenoxyacetyl)amino]-5-thia-1-azabicyclo[4.2.0]oct-2-ene-2-carboxylic acid sodium salt.

22. A compound as in claim 1 of the formula [6R-(6α,7β) (Z)]-7-[[(2-Amino-4-thiazolyl)(methoxyimino)acetyl]amino]-3-[[[1-ethyl-6-fluoro-1,4-dihydro-7-(1-pyrrolidinyl)-4-oxo-quinolin-3-yl]carbonyl]methyl]-8-oxo-5-thia-1-azabicyclo[4.2.0]oct-2-ene-2-carboxylic acid sodium salt.

23. A compound as in claim 3 of the formula [6R-[6-alpha-7-beta(Z)]]-7-[[(2-amino-4-thiazolyl)($R_{21}$oxyimino)acetyl]amino]-3-[[[[6-$R_{33}$-8-$R_{30}$-1-$R_{31}$-1,4-dihydro-7-(4-$R_{34}$-1-piperazinyl)-4-oxo-3-quinolinyl]carbonyl]oxy]methyl]-8-oxo-5-thia-1-azabicyclo[4.2.0]oct-2-ene-2-carboxylic acid and pharmaceutically acceptable salts, esters, and hydrates thereof wherein $R_{21}$ is hydrogen, lower alkyl, or a group of the formula

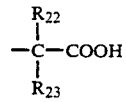

each of $R_{22}$ and $R_{23}$ are hydrogen or lower alkyl, $R_{30}$ is hydrogen or halogen; $R_{31}$ is hydrogen, lower alkyl, lower alkenyl, $C_3$–$C_7$ cycloalkyl, or 2-halo-lower-alkyl; $R_{33}$ is hydrogen or halogen; and $R_{34}$ is hydrogen or lower alkyl.

24. A compound as in claim 23 wherein $R_{21}$ is methyl.

25. A compound as in claim 24 wherein $R_{33}$ and $R_{30}$ are hydrogen or fluorine, $R_{31}$ is ethyl or 2-fluoroethyl and $R_{34}$ is methyl.

26. A compound as in claim 1 of the formula [6R-[6-alpha,7-beta]]-3-[[[[6-$R_{33}$-8-$R_{30}$-1-$R_{31}$-1,4-dihydro-7-(4-$R_{34}$-1-piperazinyl)-4-oxo-3-quinolinyl]carbonyl]oxy]methyl]-8-oxo-7-[(phenoxyacetyl)amino]-5-thia-1-azabicyclo[4.2.0]oct-2-ene-2-carboxylic acid and pharmaceutically acceptable salts thereof wherein $R_{33}$ and $R_{30}$ are hydrogen, chlorine, bromine and fluorine, $R_{31}$ is hydrogen, lower alkyl or 2-chloro-, 2-bromo- or 2-fluoroloweralkyl, and $R_{34}$ is hydrogen or lower alkyl.

27. A compound as in claim 25 wherein $R_{33}$ and $R_{30}$ are hydrogen or fluorine, $R_{31}$ is ethyl or 2-fluoroethyl and $R_{34}$ is methyl.

28. A compound as in claim 1 of the formula [6R-[6-alpha,7-beta]]-7-(formylamino)-3-[[[6-$R_{33}$-8-$R_{30}$-1-$R_{31}$-1,4-dihydro-7-(4-$R_{34}$-1-piperazinyl)-4-oxo-3-quinolinyl]carbonyl]oxy]methyl]-8-oxo-5-thia-1-azabicyclo[4.2.0]oct-2-ene-2-carboxylic acid and pharmaceutically acceptable salts thereof wherein $R_{33}$ and $R_{30}$ are hydrogen, chlorine, bromine and fluorine, $R_{31}$ is hydrogen, lower alkyl or 2-chloro-, 2-bromo- or 2-fluoroloweralkyl, and $R_{34}$ is hydrogen or lower alkyl.

29. A compound as in claim 27 wherein $R_{33}$ and $R_{30}$ are hydrogen or fluorine, $R_{31}$ is ethyl or 2-fluoroethyl and $R_{34}$ is methyl.

30. A compound as in claim 1 wherein $R_{22}$ and $R_{23}$ are both methyl.

31. A compound as in claim 29 wherein $R_{33}$ and $R_{30}$ are hydrogen or fluorine, $R_{31}$ is ethyl or 2-fluoroethyl and $R_{34}$ is methyl.

32. A compound as in claim 1 of the formula [6R-[6-alpha-7-beta(Z)]]-7-[[(2-amino-4-thiazolyl)($R_{21}$oxyimino)acetyl]amino]-3-[[[[6-$R_{33}$-8-$R_{30}$-1-$R_{31}$-1,4-dihydro-7-(4-$R_{34}$-1-piperazinyl)-4-oxo-3-quinolinyl]carbonyl]oxy]methyl]-8-oxo-5-thia-1-azabicyclo[4.2.0]oct-2-ene-2-carboxylic acid and its pharmaceutically acceptable salts wherein $R_{33}$ and $R_{30}$ are hydrogen, chlorine, bromine and fluorine, $R_{31}$ is hydrogen, lower alkyl or chloro-, bromo- or fluoroloweralkyl, $R_{34}$ is hydrogen or lower alkyl, and $R_{21}$ is the group

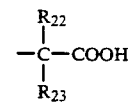

wherein $R_{22}$ and $R_{23}$ are selected from the group consisting of hydrogen and lower alkyl.

33. The compound of claim 1 wherein the acyl group is selected from the group consisting of
(a) An aliphatic group of the formula

wherein $R^5$ is selected from the group consisting of lower alkyl, lower cycloalkyl, lower alkoxy, lower alkenyl, lower cycloalkenyl, cyclohexadinenyl, or lower alkyl or lower alkenyl substituted with one or more halogen, cyano, nitro, amino, mercapto, lower alkylthio, or cyanomethylthio groups;
(b) A carbocyclic aromatic group selected from the group consisting of:

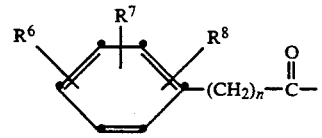

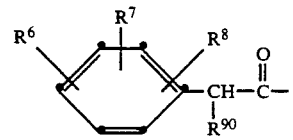

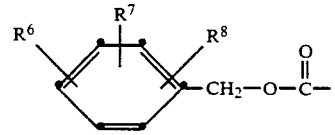

-continued

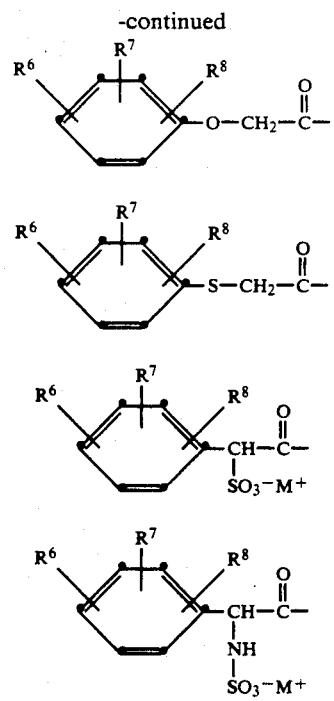

wherein n is 0, 1, 2 or 3; $R^6$, $R^7$, and $R^8$ is selected from the group consisting of hydrogen, halogen, hydroxyl, nitro, amino, cyano, trifluoromethyl, alkyl of 1 to 4 carbon atoms, alkoxy of 1 to 4 carbon atoms or aminomethyl; and $R^{90}$ is selected from the group consisting of amino, hydroxyl, a carboxyl salt, protected carboxy or azido;

(c) A heteroaromatic group selected from the group consisting of:

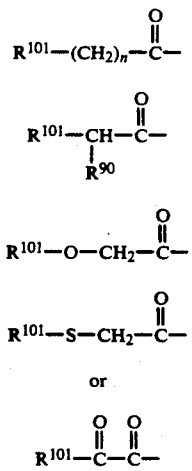

wherein n is 0, 1, 2, or 3; $R^{90}$ is as defined above; and $R^{101}$ is a substituted or unsubstituted 5-, 6-, or 7-membered heterocyclic ring containing 1, 2, 3, or 4 heteroatoms independently selected from the group consisting of nitrogen, oxygen and sulfur atoms, the remainder of the ring atoms being carbon, the heterocyclic ring being optionally substituted with halogen, hydroxyl, nitro, amino, cyano, trifluoromethyl, alkyl of 1 to 4 carbon atoms, alkoxy with 1 to 4 carbon atoms, halolower alkyl, carbamoyl, or carboxyl groups;

(d) A [[4-Substituted-2,3-dioxo-1-piperazinyl) carbonyl]amino substituted acetyl group of the formula

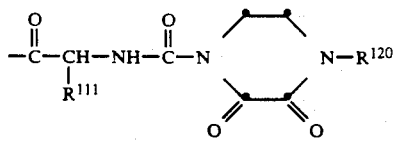

wherein $R^{111}$ is lower alkyl, hydroxy lower alkyl or an aromatic group of the formula

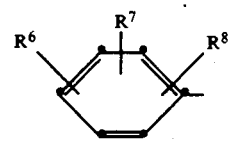

wherein $R^6$, $R^7$ and $R^8$ are as previously defined, or a heteroaromatic as defined for $R^{101}$ and $R^{120}$ is lower alkyl or substituted lower alkyl (wherein the alkyl group is substituted with one or more halogen, cyano, nitro, amino or mercapto groups);

(e) A (Substituted oxyimino) substituted acetyl group of the formula:

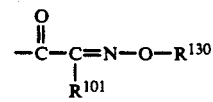

wherein $R^{101}$ is a heteroaromatic as defined above and $R^{130}$ is hydrogen, lower alkyl, $C_3$–$C_7$ cycloalkyl or substituted lower alkyl wherein the alkyl group is substituted with 1 or more halogen, cyano, nitro, amino, mercapto, lower alkylthio, aromatic group (as defined by $R^{111}$), carboxyl (including salts thereof), amido, lower alkoxycarbonyl, phenylmethoxycarbonyl, diphenylmethoxycarbonyl, hydroxyalkoxyphosphinyl, dihydroxyphosphinyl, hydroxy (phenylmethoxy) phosphinyl, or diloweralkoxyphosphinyl, carboxyl lower alkyl or carboxyl-$C_3$–$C_7$ cycloalkyl;

(f) An (Acylamino) substituted acetyl group of the formula

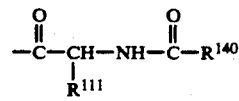

wherein $R^{111}$ is as defined above and $R^{140}$ is

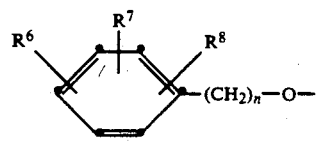

(where $R^6$, $R^7$, $R^8$ and n are previously defined), hydrogen, lower alkyl, substituted lower alkyl, amino, lower alkylamino, (cyanoloweralkyl) amino, or arylamino; and (g) A [[[3-substituted-2-oxo-1-imidazolidinyl]carbonyl]-amino] substituted acetyl group of the formula

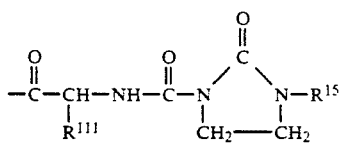

wherein $R^{111}$ is a heteroaromatic as defined above and $R^{15}$ is hydrogen, alkylsulfonyl, —N═CH—$R^{111}$ (wherein $R^{111}$ is as defined above),

(wherein $R^{16}$ is hydrogen, lower alkyl, or halogen substituted lower alkyl), aromatic group (as defined by $R^{111}$ above), lower alkyl or substituted lower alkyl (wherein the alkyl group is substituted with one or more halogen, cyano, nitro, amino or mercapto groups).

34. A compound as in claim 24 wherein $R_{33}$ and $R_{30}$ are fluorine, $R_{31}$ is 2-fluoroethyl, which is the compound [6R-[6alpha,7beta(Z)]]-7-[[(2-Amino-4-thiazolyl)(methoxyimino)acetyl]amino]-3-[[[[6,8-difluoro-1-(2-fluoroethyl)-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid.

35. A compound as in claim 24 wherein $R_{33}$ is fluorine, $R_{30}$ is hydrogen, $R_{31}$ is 2-fluoroethyl, and $R_{34}$ is methyl, which is the compound [6R-(6alpha,7beta(Z)]]-7-[[2-Amino-4-thiazolyl)(methoxyimino)acetyl]amino]-3-[[[[6-fluoro-1-(2-fluoroethyl)-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid.

36. A compound as in claim 24 wherein $R_{33}$ is fluorine, $R_{30}$ is hydrogen, $R_{31}$ is ethyl and $R_{34}$ is methyl, which is the compound [6R-[6alpha,7beta(Z)]]-7-[[(2-Amino-4-thiazolyl)(methoxyimino)acetyl]amino]-3-[[[[6-fluoro-1-ethyl-1,4-dihydro-7-(4-methyl-1-piperazinyl)-4-oxo-3-quinolniyl]carbonyl]oxy]methyl]-8-oxo-5-thia-1-azabicyclo[4.2.0]oct-2-ene-2-carboxylic acid.

37. A compound as in claim 27 wherein $R_{33}$ and $R_{30}$ are fluorine, and $R_{31}$ is 2-fluoroethyl, which is the compound [6R-[6-alpha,7-beta]]-3[[[[6,8-difluoro-1-(2-fluoroethyl)-1,4-dihydro-7-(4-methyl-1-piperazinyl)-4-oxo-3-quinolinyl]carbonyl]oxy]methyl]-8-oxo-7-[(phenoxyacetyl)amino]-5-thia-1-azabicyclo[4.2.0]oct-2-ene-2-carboxylic acid.

38. A compound as in claim 26 wherein $R_{33}$ is fluorine, $R_{30}$ is hydrogen, $R_{31}$ is 2-fluoroethyl, and $R_{34}$ is methyl, which is the compound [6R-[6-alpha,7-beta]]-3[[[[6-fluoro-1-(2-fluoroethyl)-1,4-dihydro-7-(4-methyl-1-piperazinyl)-4-oxo-3-quinolinyl]carbonyl]oxy]methyl]-8-oxo-7-[(phenoxyacetyl)amino]-5-thia-1-azabicyclo[4.2.0]oct-2-ene-2-carboxylic acid.

39. A compound as in claim 26 wherein $R_{33}$ is fluorine, $R_{30}$ is hydrogen, $R_{31}$ is ethyl, and $R_{34}$ is methyl, which is the compound [6R-[6-alpha,7-beta]]-3[[[[6-fluoro-1-ethyl-1,4-dihydro-7-(4-methyl-1-piperazinyl)-4-oxo-3-quinolinyl]carbonyl]oxy]methyl]-8-oxo-(7-[(phenoxyacetyl)amino]-5-thia-1-azabicyclo[4.2.0]oct-2-ene-2-carboxylic acid.

40. A compound as in claim 29 wherein $R_{33}$ and $R_{30}$ are fluorine, and $R_{31}$ is 2-fluoroethyl, which is the compound [6R-[6-alpha,7-beta]]-7-(formylamino)-3-[[[[6,8-difluoro-1-(2-fluoroethyl)-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid.

41. A compound as in claim 28 wherein $R_{33}$ is fluorine, $R_{30}$ is hydrogen, $R_{31}$ is 2-fluoroethyl, and $R_{34}$ is methyl, which is the compound [6R-[6-alpha,7-beta]]-7-(formylamino)-3-[[[[6-fluoro-1-(2-fluoroethyl)-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid.

42. A compound as in claim 28 wherein $R_{33}$ is fluorine, $R_{30}$ is hydrogen, $R_{31}$ is ethyl, and $R_{34}$ is methyl, which is the compound [6R-[6-alpha,7-beta]]-7-(formylamino)-3-[[[[6-fluoro-1-ethyl-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid.

43. A compound as in claim 31 wherein $R_{33}$ and $R_{30}$ are fluorine and $R_{31}$ is 2-fluoroethyl, which is the compound [6R-[6-alpha,7-beta(Z)]]-7-[[(2-amino-4-thiazolyl)[(1-carboxy-1-methylethoxy)imino]acetyl]amino]-3-[[[[6,8-difluoro-1-(2-fluoroethyl)-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid.

44. A compound as in claim 30 wherein $R_{33}$ is fluorine, $R_{30}$ is hydrogen, $R_{31}$ is 2-fluoroethyl and $R_{34}$ is methyl, which is the compound [6R-[6-alpha,7-beta(Z)]]-7-[[(2-amino-4-thiazolyl)[(1-carboxy-1-methylethoxy)imino]acetyl]amino]-3-[[[[6-fluro-1-(2-fluoroethyl)-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid.

45. A compound as in claim 30 wherein $R_{33}$ is fluorine, $R_{30}$ is hydrogen, $R_{31}$ is ethyl and $R_{34}$ is methyl, which is the compound [6R-[6-alpha,7-beta(Z)]]-7-[[(2-amino-4-thiazolyl)[(1-carboxy-1-methylethoxy)imino]acetyl]amino]-3-[[[[6-fluoro-1-ethyl-1,4-dihydro-7-(4-methyl-1-piperazinyl)-4-oxo-3-quinolinyl]carbonyl]oxy]methyl]-8-oxo-5-thia-1-azabicyclo[4.2.0]oct-2-ene-2-carboxylic acid.

* * * * *

UNITED STATES PATENT AND TRADEMARK OFFICE
CERTIFICATE OF CORRECTION

PATENT NO. : 5,147,871
DATED : September 15, 1992
INVENTOR(S) : Harry A. Albrecht, Ka-Kong Chan, Dennis D. Keith, Rudolf L. Then and Manfred Weigele It is certified that error appears in the above-identified patent and that said Letters Patent is hereby corrected as shown below:

Claim 16, column 40, line 60, delete "(Z)]-[[(Z)]-7-Amino-4-thiazolyl)" and insert therefor -- (Z)]-7-[[(2-Amino-4-thiazolyl) --;

Claim 17, column 40, line 67, delete "(Z)]-[[(2)]-7-Amino-4-thiazolyl)" and insert therefor -- (Z)]-7-[[(2-Amino-4-thiazolyl) --;

Claim 22, column 41, line 27, between "carbonyl]methyl" insert -- oxy] --;

Claim 36, column 45, line 45, change "quinolniyl" to -- quinolinyl --;

Claim 44, column 46, line 45, change "fluro" to -- fluoro --.

Signed and Sealed this

Nineteenth Day of October, 1993

Attest:

BRUCE LEHMAN

Attesting Officer    Commissioner of Patents and Trademarks